(12) United States Patent
Gruenbacher et al.

(10) Patent No.: US 9,393,337 B2
(45) Date of Patent: Jul. 19, 2016

(54) DISPENSER FOR DISPENSING VOLATILE COMPOSITIONS

(71) Applicant: The Procter & Gamble Company, Cincinnati, OH (US)

(72) Inventors: Dana Paul Gruenbacher, Fairfield, OH (US); Mark William Baize, Wyoming, OH (US); Stephan Gary Bush, Liberty Township, OH (US); Frank Peter Kressmann, Eschborn (DE); Uwe Schober, Schlossborn (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/950,491

(22) Filed: Jul. 25, 2013

(65) Prior Publication Data

US 2013/0309102 A1 Nov. 21, 2013

Related U.S. Application Data

(62) Division of application No. 12/778,578, filed on May 12, 2010, now Pat. No. 8,603,397.

(60) Provisional application No. 61/177,538, filed on May 12, 2009.

(51) Int. Cl.
*A61L 9/14* (2006.01)
*A01M 1/20* (2006.01)
*A61L 9/12* (2006.01)
*B60H 3/00* (2006.01)

(52) U.S. Cl.
CPC .............. *A61L 9/145* (2013.01); *A01M 1/2033* (2013.01); *A61L 9/122* (2013.01); *B60H 3/0028* (2013.01); *A61L 2209/111* (2013.01); *A61L 2209/133* (2013.01); *B60H 2003/0042* (2013.01)

(58) Field of Classification Search
CPC ........... A61L 9/12; A61L 9/122; A61L 9/127; A61L 9/145; A01M 1/2033; B60H 3/0028
See application file for complete search history.

(56) References Cited

U.S. PATENT DOCUMENTS 3,028,100 A 4/1962 Aurelio et al.
4,258,004 A * 3/1981 Valenzona et al. ............ 422/123
4,301,095 A * 11/1981 Mettler et al. .................. 261/30

(Continued)

FOREIGN PATENT DOCUMENTS

DE 20314349 12/2003
JP 56-001644 U 6/1979

(Continued)

OTHER PUBLICATIONS

International Search Report, dated Jul. 30, 2010.

*Primary Examiner* — Regina M Yoo
(74) *Attorney, Agent, or Firm* — Abbey A. Lopez; Amy I. Ahn-Roll

(57) ABSTRACT

A volatile composition dispenser is configured to be used in a vehicle. The volatile composition dispenser comprises a housing and a fan positioned at least partially within the housing. The fan is configured to intermittently activate to move a volume of air. The volatile composition dispenser further comprises a controller in electrical communication with the fan and positioned within the housing, and a replaceable unit configured to be attached to the housing and positioned at least partially within the housing.

16 Claims, 17 Drawing Sheets

(56) References Cited

U.S. PATENT DOCUMENTS

| | | | |
|---|---|---|---|
| 4,361,279 A * | 11/1982 | Beacham | 239/56 |
| 4,432,938 A | 2/1984 | Meetze | |
| 4,840,770 A | 6/1989 | Walz et al. | |
| 4,865,816 A | 9/1989 | Walz et al. | |
| 5,126,078 A | 6/1992 | Steiner et al. | |
| 5,133,042 A | 7/1992 | Pelonis | |
| 5,147,582 A | 9/1992 | Holzner et al. | |
| 5,304,358 A * | 4/1994 | Hoyt et al. | 422/305 |
| 5,370,829 A | 12/1994 | Kunze | |
| 5,376,338 A | 12/1994 | Zlotnik | |
| 5,431,885 A | 7/1995 | Zlotnik et al. | |
| 5,498,397 A | 3/1996 | Horng | |
| 5,547,616 A | 8/1996 | Danes et al. | |
| 5,662,835 A | 9/1997 | Collingwood | |
| 6,032,930 A | 3/2000 | Calino | |
| 6,354,513 B1 | 3/2002 | Basaganas Millan | |
| 6,371,450 B1 | 4/2002 | Davis et al. | |
| 6,592,104 B2 | 7/2003 | Cox | |
| 6,619,560 B1 | 9/2003 | Chun | |
| 6,631,888 B1 | 10/2003 | Prueter | |
| 6,938,883 B2 | 9/2005 | Adams et al. | |
| 6,966,665 B2 | 11/2005 | Limburg et al. | |
| 7,005,000 B2 | 2/2006 | Stiros et al. | |
| 7,009,519 B2 | 3/2006 | Leonard et al. | |
| 7,032,831 B2 | 4/2006 | Duston et al. | |
| 7,210,812 B1 | 5/2007 | Linton | |
| 7,244,398 B2 | 7/2007 | Kotary et al. | |
| 7,282,248 B2 | 10/2007 | Asano et al. | |
| 7,350,720 B2 | 4/2008 | Jaworski et al. | |
| 7,462,329 B2 | 12/2008 | Wefler | |
| 7,484,716 B2 | 2/2009 | Ford Morie et al. | |
| 7,499,632 B2 | 3/2009 | Granger et al. | |
| 7,503,668 B2 * | 3/2009 | Porchia et al. | 362/161 |
| 7,540,473 B2 | 6/2009 | Schwarz | |
| 2003/0051387 A1 * | 3/2003 | Rodgers | 43/1 |
| 2004/0033171 A1 | 2/2004 | Kvietok et al. | |
| 2004/0265196 A1 | 12/2004 | Varanasi et al. | |
| 2005/0185392 A1 | 8/2005 | Walter et al. | |
| 2005/0244307 A1 | 11/2005 | Gygax et al. | |
| 2007/0122306 A1 | 5/2007 | Brown et al. | |
| 2007/0183940 A1 | 8/2007 | Yamamoto et al. | |
| 2007/0217945 A1 * | 9/2007 | Selander | 422/5 |
| 2007/0257130 A1 * | 11/2007 | Butler | A01M 1/2033 239/47 |
| 2007/0258865 A1 * | 11/2007 | Yamasaki et al. | 422/124 |
| 2008/0164337 A1 | 7/2008 | Brown et al. | |
| 2008/0169360 A1 | 7/2008 | Brown et al. | |
| 2008/0311008 A1 | 12/2008 | Tranzeat | |
| 2009/0008411 A1 | 1/2009 | Schumacher et al. | |
| 2010/0038443 A1 | 2/2010 | Pankhurst et al. | |
| 2010/0269826 A1 * | 10/2010 | Colombo et al. | 128/203.26 |
| 2010/0288847 A1 | 11/2010 | Gruenbacher et al. | |
| 2011/0221079 A1 * | 9/2011 | Yamasaki et al. | 261/135 |

FOREIGN PATENT DOCUMENTS

| | | |
|---|---|---|
| JP | 57123148 A | 7/1982 |
| JP | S59-146022 U | 9/1984 |
| JP | S60-06337 U | 5/1985 |
| JP | 2005185139 A | 7/2005 |
| JP | 2009000041 A | 1/2009 |
| WO | WO 88/08721 A1 | 11/1988 |
| WO | WO 2009/018862 A1 | 2/2009 |
| WO | WO 2009/071666 | 6/2009 |

* cited by examiner

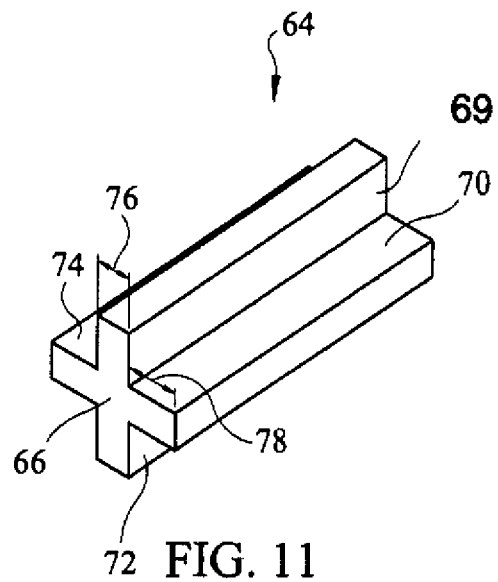
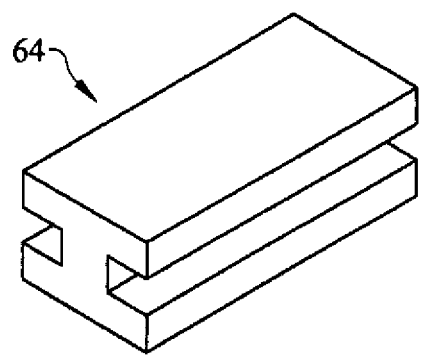
FIG. 11
FIG. 12
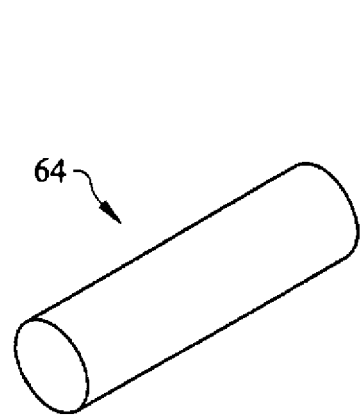
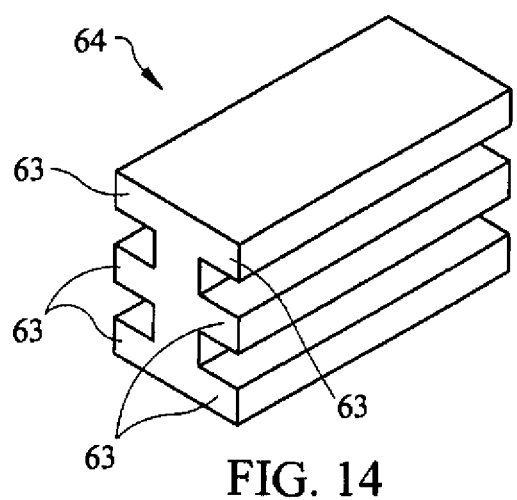
FIG. 13
FIG. 14

US 9,393,337 B2

DISPENSER FOR DISPENSING VOLATILE COMPOSITIONS

FIELD

The present disclosure relates to methods and apparatuses for dispensing volatile compositions and, more particularly, relates to methods and apparatuses for dispensing volatile compositions using an actuator.

BACKGROUND

An air freshener can be used to provide a pleasant scent to an area surrounding the air freshener. In certain circumstances, air fresheners can be used in vehicles. Various air fresheners can provide a constant emission of a volatile composition, such as a fragrance, to an interior atmosphere of a vehicle, regardless of whether the vehicle is operating or dormant. Such constant emission of the volatile composition can cause passengers to become acclimated to the volatile composition, thereby essentially rendering the air freshener useless. Further, in some instances, temperatures within the interior atmosphere of the vehicle can be extreme leading to a volatile composition scent that can be either too powerful or not noticeable to the passengers of the vehicle. What is needed is an improvement over the foregoing.

SUMMARY

In one non-limiting embodiment of the present disclosure, a volatile composition dispenser is configured to be used in a vehicle. The volatile composition dispenser comprises a housing and a fan positioned at least partially within the housing. The fan is configured to intermittently activate to move a volume of air. The volatile composition dispenser further comprises a controller in electrical communication with the fan and positioned within the housing, and a replaceable unit configured to be one of attached to the housing and positioned at least partially within the housing. The replaceable unit comprises a volatile composition container comprising a volatile composition in at least partially a liquid phase and configured to evaporate into a vapor phase. The fan is configured to intermittently force the volume of air at least partially through the volatile composition container to expel at least most of the vapor phase volatile composition into an atmosphere of a vehicle. The replaceable unit further comprises a power source in electrical communication with the controller.

In another non-limiting embodiment of the present disclosure, a volatile composition dispenser comprises a centrifugal fan configured to intermittently move a volume of air and a controller operably engaged with the centrifugal fan. The volatile composition dispenser further comprises a volatile composition container comprising a volatile composition in at least one of a liquid phase and a vapor phase. The volatile composition container is configured to receive at least most of the volume of air. The volatile composition container further comprises a material comprising at least one surface. The material is configured to at least partially inhibit the volatile composition from transforming from the liquid phase into the vapor phase. A flow path of the volume of air at least partially through the volatile composition container is substantially along the at least one surface of the material.

In still another non-limiting embodiment of the present disclosure, a volatile composition dispenser comprises a housing and a centrifugal fan positioned within the housing. The centrifugal fan is configured to be intermittently activated to move a volume of air. The volatile composition dispenser further comprises a controller in electrical communication with the centrifugal fan and positioned within the housing, and a volatile composition container. The volatile composition container comprises an inner wall, at least one projection extending from the inner wall, and a material configured to contain a volatile composition in at least partially a liquid phase. The at least one projection is configured to engage a portion of the material to maintain the portions of the material at a distance away from the inner wall. In various embodiments the use of projection is optional. The volatile composition container further comprises a space defined intermediate the inner wall and the portions of the material. At least a portion of the liquid phase volatile composition is configured to evaporate into the space to create a saturated vapor phase volatile composition within the space. The centrifugal fan is configured to intermittently force the volume of air at least partially through the space to expel at least most of the saturated vapor phase volatile composition from the volatile composition container.

In yet another non-limiting embodiment of the present disclosure, a replaceable unit for a volatile composition dispenser comprising a centrifugal fan configured to be intermittently activated is provided. The replaceable unit comprises a volatile composition container comprising an inner wall, at least one projection extending from the inner wall, and a material configured to contain a volatile composition in at least partially a liquid phase. The at least one projection is configured to engage a portion of the material to maintain the material at a distance away from the inner wall. The replaceable unit further comprises a space defined intermediate the inner wall and the material. At least a portion of the liquid phase volatile composition is configured to evaporate into the space to create a saturated vapor phase volatile composition within the space. The replaceable unit further comprises a power source configured to provide power to the centrifugal fan.

In yet another non-limiting embodiment of the present disclosure, a method of dispensing a volatile composition comprises providing a replaceable unit comprising a power source and a volatile composition container comprising a volatile composition. The method further comprises providing a centrifugal fan powered by the power source and in fluid communication with the volatile composition container, evaporating a portion of the volatile composition within the volatile composition container, and using the centrifugal fan to intermittently force a volume of air at least partially through the volatile composition container to expel at least most of the evaporated portion of the volatile composition from the volatile composition container.

BRIEF DESCRIPTION OF DRAWINGS

The above-mentioned and other features and advantages of the present disclosure, and the manner of attaining them, will become more apparent and the present disclosure itself will be better understood by reference to the following description of various non-limiting embodiments of the present disclosure taken in conjunction with the accompanying drawings, wherein:

FIG. 11 is a perspective view of a material configured to be positioned within a volatile composition container in accordance with one non-limiting embodiment;

FIG. 12 is a perspective view of another material configured to be positioned within a volatile composition container in accordance with one non-limiting embodiment;

FIG. 13 is a perspective view of yet another material configured to be positioned within a volatile composition container in accordance with one non-limiting embodiment;

FIG. 14 is a perspective view of still another material configured to be positioned within a volatile composition container in accordance with one non-limiting embodiment;

DETAILED DESCRIPTION

Figure 1:
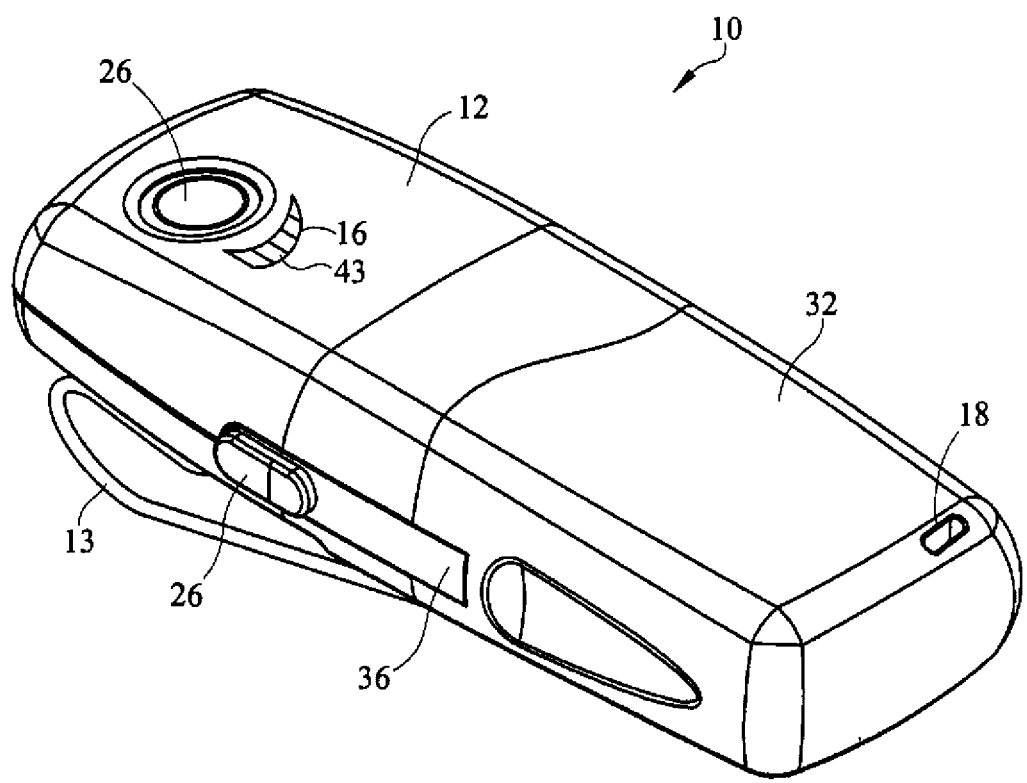
FIG. 1 is a perspective view of a volatile composition dispenser in accordance with one non-limiting embodiment.

Various embodiments will now be described to provide an overall understanding of the principles of the structure, function, manufacture, and use of the apparatuses and methods disclosed herein. One or more examples of these embodiments are illustrated in the accompanying drawings. Those of ordinary skill in the art will understand that the apparatuses and methods specifically described herein and illustrated in the accompanying drawings are non-limiting example embodiments and that the scope of the various embodiments of the present disclosure is defined solely by the claims. The features illustrated or described in connection with one example embodiment can be combined with the features of other example embodiments. Such modifications and variations are intended to be included within the scope of the present disclosure.

According to various embodiments, a volatile composition dispenser can be used to dispense a volatile composition and/or other solution or composition, such as a fragrance or an insecticide, for example, to an area surrounding the dispenser. In certain embodiments, the volatile composition can comprise a single chemical and/or a single material that is capable of entering the vapor phase or, more commonly, the volatile composition can comprise a mixture of chemicals and/or materials that are capable of entering the vapor phase. In one non-limiting embodiment, the volatile composition can also comprise non-vaporizable components in addition to vaporizable components, for example. In various embodiments, the volatile compositions can comprise, but are not limited to, substances that can function as air fresheners, deodorants, odor neutralizing materials, odor blocking materials, odor masking materials, aromatherapy materials, aromachology materials, insecticides, and/or combinations thereof. In other various embodiments, the volatile compositions can comprise other materials that can act in their vapor phase to modify, enhance, and/or treat an atmosphere or an environment. In one non-limiting embodiment, the volatile composition dispenser can be configured for use within an interior space, compartment, area, and/or atmosphere of a vehicle, for example, although the present disclosure is not limited to such use. The term "vehicle" can include a car, a van, an SUV, a truck, a train, a boat, and/or a plane, for example, or any other suitable apparatus for transporting people or things. While the volatile composition dispenser will be discussed herein with reference to use within a vehicle, those of skill in the art will understand that the volatile composition dispenser can be configured for use in any environment, such as a domestic environment, for example, and can be configured to dispense any suitable solutions, chemical, materials, and/or compositions.

In various embodiments, the volatile composition dispensed by the volatile composition dispenser and can comprise any suitable solution, chemical, material, and/or composition configured to make the interior atmosphere of the vehicle smell more pleasant to passengers and/or provide passengers with a good open door experience when entering the vehicle, for example. The volatile composition dispenser can evaporate a pleasant fragrance and/or evaporate a volatile composition that can neutralize and/or at least partially eliminate malodors, for example. In one non-limiting embodiment, the volatile composition dispenser can be configured to intermittently and/or periodically, over predetermined time intervals, provide a dose of the volatile composition to the interior atmosphere of the vehicle to prevent, or at least inhibit, the passengers of the vehicle from becoming acclimated to the smell of the volatile composition over a period of time. In such an embodiment, by selectively and/or intermittently dosing the volatile composition within the interior atmosphere of the vehicle, the passenger's sense of smell may be more aware of the volatile composition when it is dispensed. Optimal dosing time intervals and dosing amounts can vary depending on various conditions within the interior atmosphere of the vehicle, such as temperature, humidity, volume, and/or air flow conditions, for example.

When a passenger enters a vehicle having a dispenser that provides a constant dose and/or that constantly evaporates a volatile composition, the passenger can be overwhelmed by and/or not aware of the dispensed volatile composition because of the extreme conditions, such as temperature, for example, that can occur within the interior atmosphere of the vehicle. In various circumstances, volatile compositions can evaporate faster at higher temperatures and slower at lower temperatures. In some instances, the temperature in the interior atmosphere of a vehicle can get as high as 170 degrees Fahrenheit and as low as below freezing. If the same amount of a volatile composition was dispensed at each extreme of the large temperature range, a passenger could be significantly overpowered by the volatile composition at the higher temperature extreme and may not even notice and/or smell the volatile composition at the lower temperature extreme. As a result, a volatile composition dispenser that provides volatile composition dosing that is correlated to the temperature conditions or other various conditions of the interior atmosphere of the vehicle can be quite useful. In various embodiments, a smaller volatile composition dose amount can be provided by the dispenser at higher temperatures, while a larger volatile composition dose amount can be provided by the dispenser at lower temperatures, for example. In one non-limiting embodiment, a volatile composition dispenser can comprise a temperature sensor configured to determine the temperature within the interior atmosphere of the vehicle, such that the volatile composition dispenser can selectively dose the interior atmosphere of the vehicle appropriately for particular temperature conditions.

Figure 2:
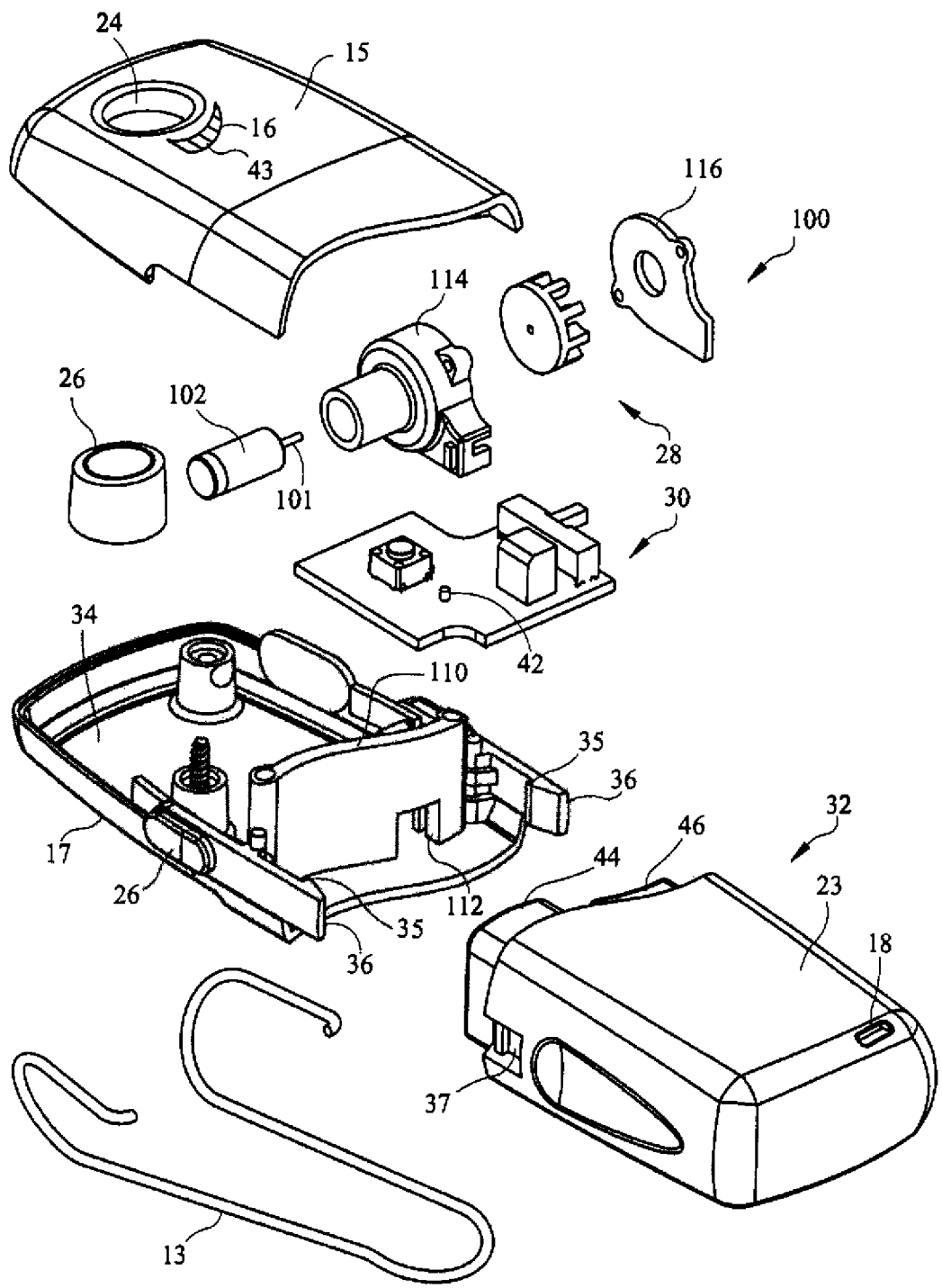
FIG. 2 is an exploded perspective view of the volatile composition dispenser of FIG. 1, illustrating various components, in accordance with one non-limiting embodiment.
Figure 3:
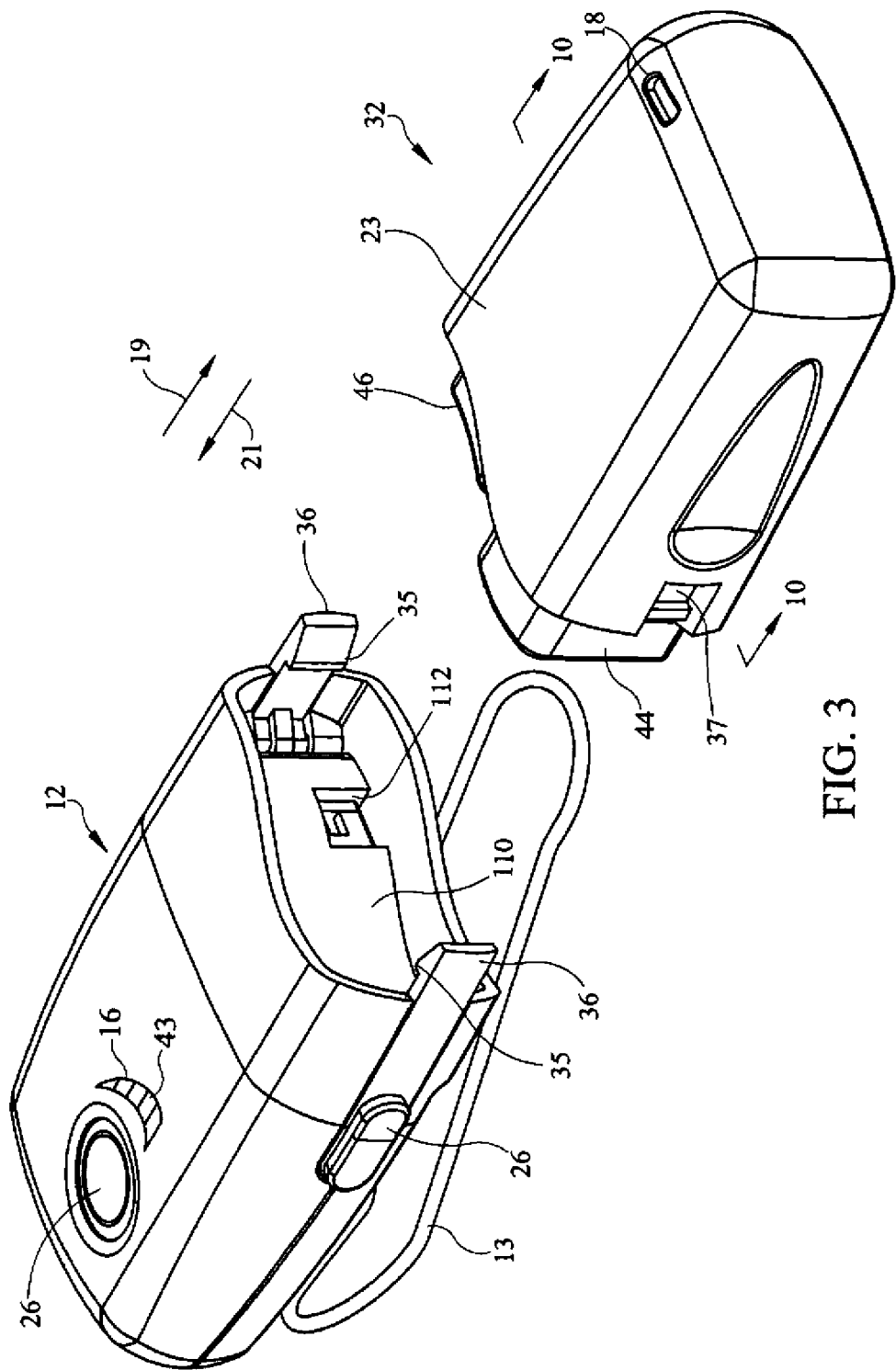
FIG. 3 is an exploded perspective view of the volatile composition dispenser of FIG. 1 in accordance with one non-limiting embodiment.

In various embodiments, referring to FIGS. 1-3, a volatile composition dispenser 10 can achieve the advantages discussed above, among other advantages, and can comprise a housing 12 and a selectably attachable replaceable unit 32. In one non-limiting embodiment, the housing 12 can comprise a user feedback module 16, such as a visible indicator, a light source, and/or an audible alert, for example. In various embodiments, the volatile composition dispenser 10 can also comprise at least one orifice 18 configured to dispense a volatile composition therethrough to an interior atmosphere of a vehicle and at least one aperture 24 configured to receive user input buttons or switches 26 therein, for example. In various embodiments, the housing 12 can comprise an elongate shape or any other suitable shape configured to accept the various internal components discussed herein. In one non-limiting embodiment, referring to FIG. 2, the housing 12 can comprise a top shell 15 and a bottom shell 17. The top shell 15 can be attached to the bottom shell 17 using any suitable attachment method, such as adhesive bonding or a mechanical connection, for example. The volatile composition dispenser 10 can also comprise a clip 13 formed with or attached to the housing 12 or other suitable portion of the volatile composition dispenser 10. In one non-limiting embodiment, the clip 13 can be used to attach the volatile composition dispenser 10 to a visor, an air vent within a vehicle, and/or to another object, for example.

Figure 6:
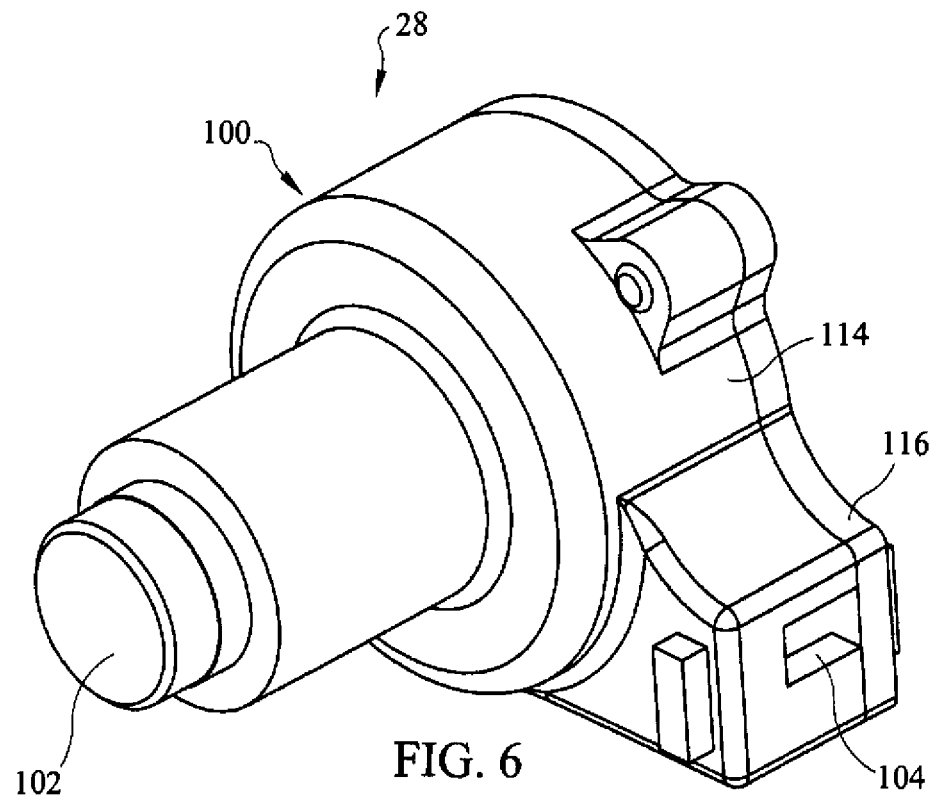
FIG. 6 is a perspective view of an actuator of a volatile composition dispenser in accordance with one non-limiting embodiment.
Figure 7:
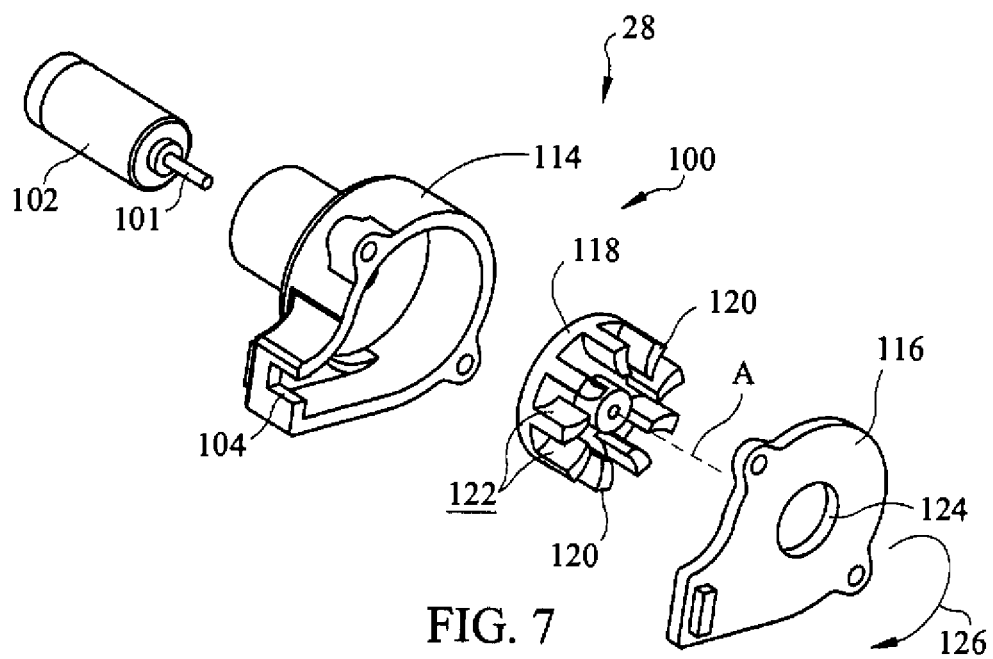
FIG. 7 is an exploded perspective view of the actuator of FIG. 6 in accordance with one non-limiting embodiment.

In various embodiments, referring to FIGS. 1, 6, and 7, the housing 12 can be configured to receive various internal components of the volatile composition dispenser 10. In one non-limiting embodiment, the various internal components can comprise an actuator 28 configured to provide a volume, a volumetric displacement, a pulse, a stream, a flow, a bolus, and/or a puff (hereafter "volume") of air or other suitable fluid or gas (hereafter "air"), and a controller 30. In such an embodiment, if the replaceable unit 32 is connected to the housing 12 as shown in FIG. 1, the actuator 28 can be in fluid communication with a portion of the replaceable unit 32 such that it can provide at least most of the volume of air to a portion of the replaceable unit 32. In one non-limiting embodiment, the housing 12 can define a receiving portion 34 configured to receive various internal components, such as the actuator 28 and the controller 30, for example. In other various embodiments, the housing 12 can define one receiving space configured to receive all of the various internal components or can comprise a separate receiving space for each of the various internal components, for example.

In one non-limiting embodiment, referring to FIGS. 2-5 the housing 12 can comprise at least one latch 36 attached thereto or formed therewith. The latch 36 can extend from the housing 12 in any suitable direction. In one non-limiting embodiment, the latch 36 can be configured to selectively attach the replaceable unit 32 to the housing 12 when the replaceable unit 32 is moved toward the housing 12 in a direction indicated by arrow 21. The latch 36 can be configured to release the replaceable unit 32 from the housing 12 when the replaceable unit 32 is moved away from the housing 12 in a direction indicated by arrow 19. In various embodiments, the latch 36 can comprise a tooth 35 configured to engage a slot 37 on the replaceable unit 32 or on the portion of the housing 12 of the replaceable unit 32. In one non-limiting embodiment, a latch, like latch 35, can be formed integral with or attached to the replaceable unit 32 and can engage a slot, like slot 37, on the housing 12. As will be appreciated by those of skill in the art, other attachment techniques and/or latch designs can be used to secure the replaceable unit 32 to the housing 12, such as other attachment members, a threaded connection, a friction/compression connection, and/or a magnetic connection, for example. In one non-limiting embodiment, a housing (not illustrated) can comprise a cavity configured to receive a replaceable unit, such as the replaceable unit 32' illustrated in FIG. 4A, for example, and a movable door (not illustrated) that can be opened to remove and/or replace the replaceable unit 32'. For example, after a new replaceable unit 32' is inserted into a cavity of the housing, the movable door can be closed to complete the circuit of the power source 38 with the controller 30, as the movable door can comprise an electrically conductive portion configured to engage a terminal of the power source 38.

In various embodiments, referring to FIGS. 1-4, and 5-7, the replaceable unit 32 can comprise a shell 23. The shell 23 can define a volatile composition container 50 and a power source receiving space 52. In one non-limiting embodiment, referring to FIG. 4, the volatile composition container 50 and the power source receiving space 52 can be separated by a wall 54. In other embodiments, the wall 54 can be eliminated. In one non-limiting embodiment, the power source receiving space 52 can be configured to receive a power source 38. In one non-limiting embodiment, referring to FIG. 5, the power source receiving space 52 can comprise an electrical lead 51 configured to transmit power from the power source 38 to the controller 30 and/or configured to complete the electrical circuit of the power source 38 with the controller 30. In one non-limiting embodiment, referring to FIG. 4, as discussed in the further detail below, the volatile composition container 50 can be configured to receive a high surface area material 64 containing a volatile composition. The high surface area material 64 can be sealably received by the volatile composition container 50.

In various non-limiting embodiments the high surface area material 64 may have a volume of about 2 $cm^3$ to about 16 $cm^3$ or alternatively of about 5 $cm^3$ to about 12 $cm^3$ and an evaporative surface area (i.e.; the surface area of the high surface area material exposed to air flow) of about 5 $cm^2$ to about 50 $cm^2$ or alternatively of about 15 $cm^2$ to about 45 $cm^2$. The high surface area material 64 may contain a volatile composition wherein the volume of volatile composition within the high surface area material 64 may be from about 1.5 ml to about 12 ml or alternatively, from about 4 ml to about 10 ml.

Figure 4:
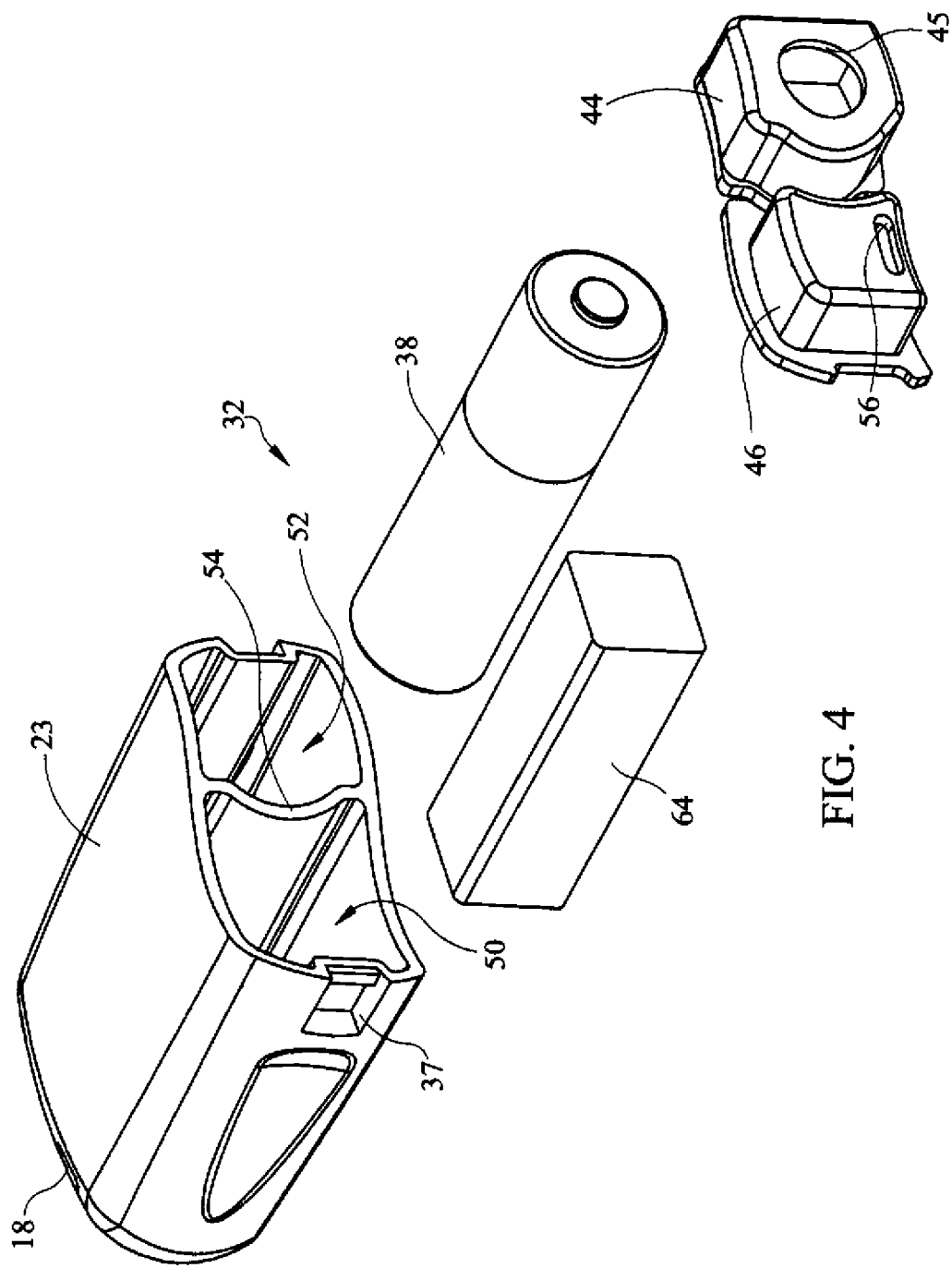
FIG. 4 is an exploded perspective view of a replaceable unit of a volatile composition dispenser in accordance with one non-limiting embodiment.
Figure 4A:
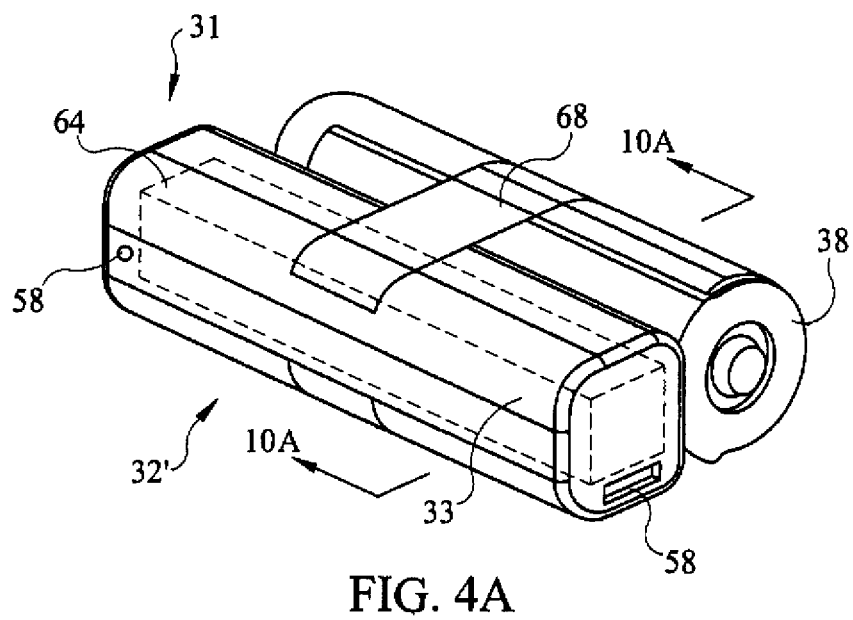
FIG. 4A is a perspective view of a replaceable unit of a volatile composition dispenser in accordance with one non-limiting embodiment.

In one non-limiting embodiment, as illustrated in FIG. 4A, the high surface area material 64 can be sealably contained within a volatile composition container 33. In such an embodiment, the volatile composition container 33 can be formed with or otherwise secured to the power source 38 by a strap 68, for example, to form a replaceable unit 32'. In various embodiments, the power source 38 can be attached to the volatile composition container 33 using any suitable technique, such as any suitable clip, clamp, band, adhesive, and/or sleeve, for example. In one non-limiting embodiment, although not illustrated, a housing can be configured to receive the replaceable unit 32'. In such an embodiment, the replaceable unit 32 will not be used with the volatile composition dispenser 10. The volatile composition container 33 can have two or more orifices 58 to allow the volume of air to flow into and through the volatile composition container 33 when located proximate to the actuator 28 within the housing. The two or more orifices 58 defined by volatile composition container 33 can comprise at least one inlet orifice and at least one outlet orifice. The at least one outlet orifice can be in fluid communication with outlet orifice 18. As will be appreciated by those of skill in the art, the two or more orifices 58 can be covered when the replaceable unit 32' is not in use to avoid diffusion and evaporative losses of the volatile composition. In other embodiments, the two or more orifices 58 can be sized and configured to at least inhibit evaporative losses of the volatile composition within the volatile composition container 33.

In various embodiments, the replaceable units 32 or 32' can allow for renewal of the volatile composition dispenser 10 without replacement of the controller 30, the actuator 28, and/or the entire volatile composition dispenser 10 itself. For example, the replaceable unit 32 or 32' can be replaced with a different replaceable unit 32 or 32'. Those of skill in the art will recognize that the replaceable unit 32' will be inserted into a housing (not illustrated) and that the replaceable unit 32 will be attached to the housing 12. In some embodiments, the replaceable unit 32' can be inserted into a shell 23 and attached to the housing 12. Hereafter, the replaceable unit 32 and the replaceable unit 32' will be referred to as "replaceable unit 32", unless otherwise noted.

In various embodiments, the replaceability of the replaceable unit 32 can also allow the user to easily change from dispensing one volatile composition to another volatile composition in a safe, substantially leak-free, and simple manner. In some instances, the user can have difficulty determining when to replace the volatile composition container and/or the power source 38 in the volatile composition dispenser 10. In various circumstances, the life of a volatile composition within the volatile composition container can be extended or shortened based on various operating and/or environmental conditions that the volatile composition dispenser 10 is exposed to, such as ambient air temperature, for example. In one non-limiting embodiment, by providing a replaceable unit having both a volatile composition container and a power source, the user does not now have to "guess" when the volatile composition is expired and/or is at least mostly expired and can merely rely on the power level of the power source 38 to determine when replacement of the replaceable unit 32 is required. In various embodiments, the controller 30 can measure the voltage, the amperage, and/or the remaining power level of the power source 38, for example, and can indicate to the user, through the user feedback module 16, when replacement of the replaceable unit 32 is required. In one non-limiting embodiment, by providing the replaceable unit 32, the volatile composition dispenser 10 can operate at a high level of efficiency in that the volatile composition container 33 or 50 will usually have an adequate amount of volatile composition therein and the power source 38 will usually be able to provide adequate power to the volatile composition dispenser 10 to maintain the desired delivery rate of the volatile composition. Additionally, the replaceable unit 32 can possibly prevent, or at least inhibit, the requirement for separate replacement of a power source and/or a volatile composition container, which could cause delivery of the volatile composition below desired levels, owing to either an inadequate power level in the power source and/or an inadequate amount of volatile composition remaining within the volatile composition container. The replaceable unit 32 solves these issues by providing a fresh power source 38 and a fresh volatile composition container 33 or 50 containing a fresh volatile composition each time the replaceable unit 32 is replaced by a user.

In various embodiments, the power source 38 can comprise a battery, such as a AA battery, a AAA battery, a 9 volt battery, and/or other suitable battery, for example. In one non-limiting embodiment, the replaceable unit 32 can be disposable and can be configured to prevent, or at least inhibit, leakage of the volatile composition therefrom. In various embodiments, the power source 38 can provide power to the controller 30, such that the controller 30 can power the actuator 28, the user feedback module 16, a temperature sensor, an air flow sensor, a motion sensor, and/or various other sensors, for example. In various embodiments, the replaceable unit 32 can comprise a power source cap 44 and a volatile composition container cap 46. In various embodiments, the volatile composition container cap 46 has a sealed engagement with the volatile composition container 50. In one non-limiting embodiment, referring to FIG. 4, the power source cap 44 can define a port 45 configured to receive at least a terminal of the power source 38. In one non-limiting embodiment, the power source cap 44 can be electrically conductive. The power source cap 44, or a portion of the power source 38, can be configured to be in electrical communication with the controller 30 when the replaceable unit 32 is attached to the housing 12 in order to complete an electrical circuit of the power source 38. In other various embodiments, the power source 38 can be in electrical communication with other various internal components positioned within the receiving portion 34 in any suitable fashion known to those skilled in the art.

Further to the above, in still other various embodiments, the volatile composition dispenser 10 can be powered by a power source of the vehicle, such as a cigarette lighter plug or an auxiliary power port, for example. In one non-limiting embodiment, a solar power source, such as a solar cell, for example, can be used to power the volatile composition dispenser 10. In various embodiments, the solar cell (i.e., a photovoltaic cell) can be positioned on an outer portion of the volatile composition dispenser 10 or in communication with the volatile composition dispenser 10, such that the solar cell can receive light that can be transformed into energy to power the volatile composition dispenser 10. In other various embodiments, the volatile composition dispenser 10 can comprise an electrical cord in electrical communication with the controller 30 or other components of the volatile composition dispenser 10, such that when the electrical cord is plugged into a conventional electrical outlet, the controller 30 can be powered. In one non-limiting embodiment, the power source 38 can be a rechargeable power source that can be recharged using any suitable technique. Those of skill in the art, upon review of the present disclosure, will recognize that any other suitable method or device can be used to provide power to the volatile composition dispenser 10.

In various embodiments, referring to FIGS. 1-5 the replaceable unit 32 can comprise an inlet orifice 56 and the outlet orifice 18, for example. If the replaceable unit 32' is provided, the volatile composition container 33 can have at least one outlet orifice 58 proximate to its distal end 31, for example. In one non-limiting embodiment, referring to FIGS. 2, 6, and 7, the actuator 28 can be in fluid communication with the inlet orifice 56 of the volatile composition container cap 46 such that the actuator 28 can provide the volume of air to the inlet orifice 56. In one non-limiting embodiment, the actuator 28 can force the volume of air through the inlet orifice 56 and at least partially through the length of the volatile composition container 50 to cause at least a portion of the volume of air to exit the volatile composition dispenser 10 volatile composition container 50 is configured to be used with the volatile composition dispenser 10. In various embodiments, the inlet orifice 56 and outlet orifice 18 can comprise a tube-like configuration, comprising an inner diameter (ID) and a length (L). In various embodiments, the cross sectional area of inlet orifice 56 and/or outlet orifice 18 may be circular, oblong, rectangular, for example, or can have any other suitable configuration. The inlet orifice 56 and the outlet orifice 18 may comprise tube-like configurations of similar dimensions. In other embodiments, the tube-like configuration of the inlet orifice 56 may differ from the tube-like configuration of the outlet orifice 18. For example, the length of inlet orifice 56 may be less than the length of the outlet orifice 18. In various embodiments, the inlet orifice 56 and/or the outlet orifice 18 may comprise passages or channels, for example, or any other suitable configurations for allowing the passage of the volume of air.

Figure 9:
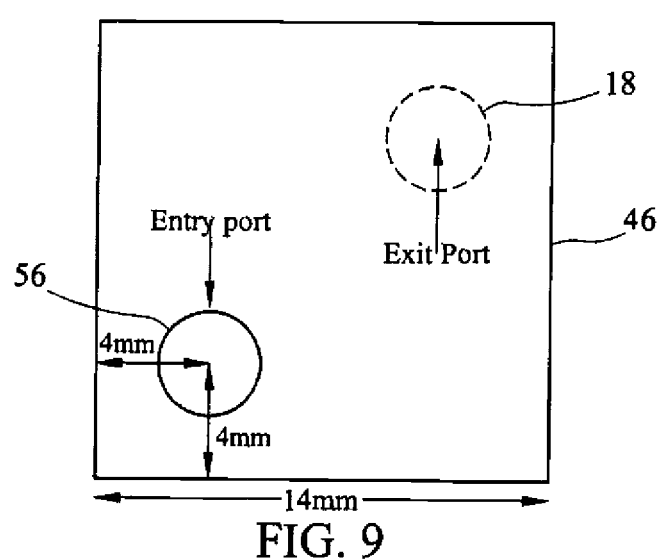
FIG. 9 is another end view of a volatile composition container configured to be used with a volatile composition dispenser in accordance with one non-limiting embodiment.

Furthermore, referring to FIG. 9, the outlet orifice 18 can be offset with respect to a central longitudinal axis from the inlet orifice 56, to create a tortuous path through the volatile composition container 50. As will be appreciated by those of skill in the art after considering the present disclosure, the location and size of the inlet and outlet orifices can be altered to achieve the desired flow rates, pressure drops, and other flow characteristics through the volatile composition containers 33 and 50. Example flow rates for non-limiting embodiments are provided in Table 1 below. For the purposes of this example, and in accordance with various embodiments, the high surface area material 64 is centered in container with a 2 mm gap between the high surface area material 64 and the inner wall of the volatile composition container 50 to allow for air flow through the volatile composition container 50.

TABLE 1

| Fan Supply Voltage | Approximate Fan speed | Inlet orifice 56 inner diameter/length | Inlet orifice 18 inner diameter and length | Volatile composition container 50 size | Flow rate |
|---|---|---|---|---|---|
| 0.7 VDC | 5500 RPM | 2.5 mm ID/10 mm length | Three 1 mm diameter holes each .5 mm length | 14 mm × 14 mm × 54 mm long | 5.7 ml/sec |
| 0.7 VDC | 5500 RPM | 2.5 mm ID/10 mm length | 2.5 mm ID/10 mm length | 14 mm × 14 mm × 54 mm | 5.1 ml/sec |
| 0.7 VDC | 5500 RPM | 1.5 mm ID/10 mm length | 1.5 mm ID/10 mm length | 14 mm × 14 mm × 54 mm | 2.7 ml/sec |
| 1.1 VDC | 94 00 RPM | 2.5 mm ID/10 mm length | 2.5 mm ID/10 mm length | 14 mm × 14 mm × 54 mm | 13 ml/sec | through the outlet orifice 18. The purpose of forcing the volume of air through the volatile composition container 50 is to force at least a portion, or in some instances most of, a vapor phase volatile composition from the volatile composition container 50. In various embodiments, the diameter, perimeter, cross-sectional configuration, and/or length of the inlet orifice 56 can be sized, shaped, and/or configured to minimize pressure losses across the volatile composition container 50.

Figure 8:
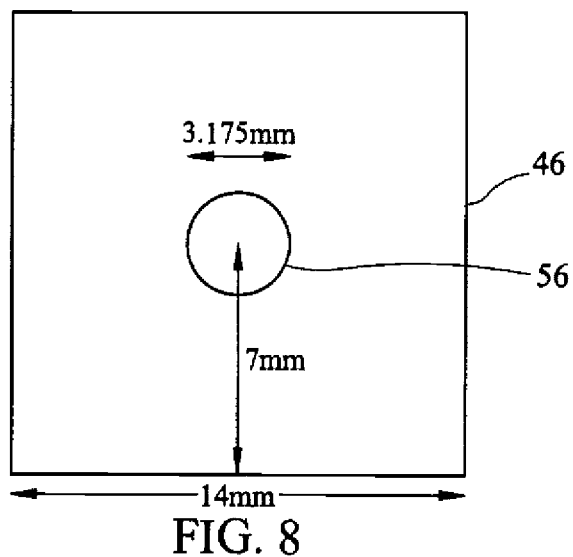
FIG. 8 is an end view of a volatile composition container configured to be used with a volatile composition dispenser in accordance with one non-limiting embodiment.
Figure 8A:
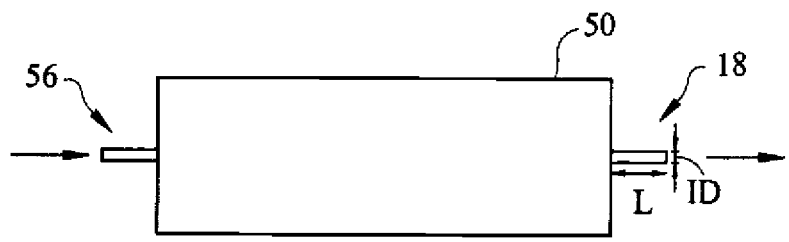
FIG. 8A is side view of a volatile composition container configured to be used with a volatile composition dispenser in accordance with one non-limiting embodiment.

In one non-limiting embodiment, referring to FIG. 8, the inlet orifice 56 can, for example, be generally centered on a face of the volatile composition container cap 46. In other embodiments, referring to FIG. 9, the inlet orifice 56 can be positioned at a location proximate to a side portion of the face of the volatile composition container cap 46. Referring to FIG. 8, the orifice 56 can also be located in any suitable location on volatile composition container 50. In one non-limiting embodiment, referring to FIG. 8A, a side view of an example volatile composition container 50 is provided. The In one non-limiting embodiment, the volatile composition container 50 of the replaceable unit 32 can comprise a plurality of inlet orifices 56 and a single outlet orifice 18. In other embodiments, the replaceable unit 32 can comprise a single inlet orifice 56 and a plurality of outlet orifices. In still other embodiments, the replaceable unit 32 can comprise a plurality of inlet orifices 56 and a plurality of outlet orifices 18. In one non-limiting embodiment, referring to FIG. 4, the inlet orifice 56 can be generally rectangular and located proximate to a side wall of the volatile composition container 50 and/or on the cap 46 of the volatile composition container 50. In various embodiments, referring to FIG. 4A, if a volatile composition container 33 is employed to house the volatile composition, the volatile composition container cap 46 can be eliminated as the actuator 28 can deliver the air directly to an inlet orifice 58 when the volatile composition container 33 is positioned within the housing (not illustrated).

In various embodiments, however, the inlet orifices of the volatile composition containers 33 and 50 can include other shapes, such as circular, elongate, square, triangular, for example, or other suitable shape configured to receive the volume of air from the actuator 28. The inlet orifice 56 can also be located in other suitable locations on the volatile composition container cap 46, such as centered or offset from a centerline (in a longitudinal direction) of volatile composition container 50. The inlet orifice 58 can also be located in other suitable locations on the volatile composition container 33, such as centered or offset from a centerline (in a longitudinal direction) of the volatile composition container 33. Furthermore, the diameter, perimeter, and/or length of the outlet orifices, such as orifices 18 and 58, for example, can be sized, shaped, and/or configured to minimize pressure losses from the actuator 28 into the volatile composition container 33 or 50 and at least inhibit evaporation of the volatile composition from the volatile composition containers 33 and 50. In various embodiments, the volume of air forced through the volatile composition container 33 or 50 can cause the volatile composition dispenser 10 to dispense at least a portion of the volume of air and at least a portion of a vapor phase volatile composition situated within the volatile composition container 33 or 50 through the outlet orifice 18 and to the interior atmosphere of the vehicle. In various embodiments, the interior atmosphere of the vehicle can be a passenger compartment, a trunk, a storage space, an enclosed space, and/or another space, for example.

Figure 5:
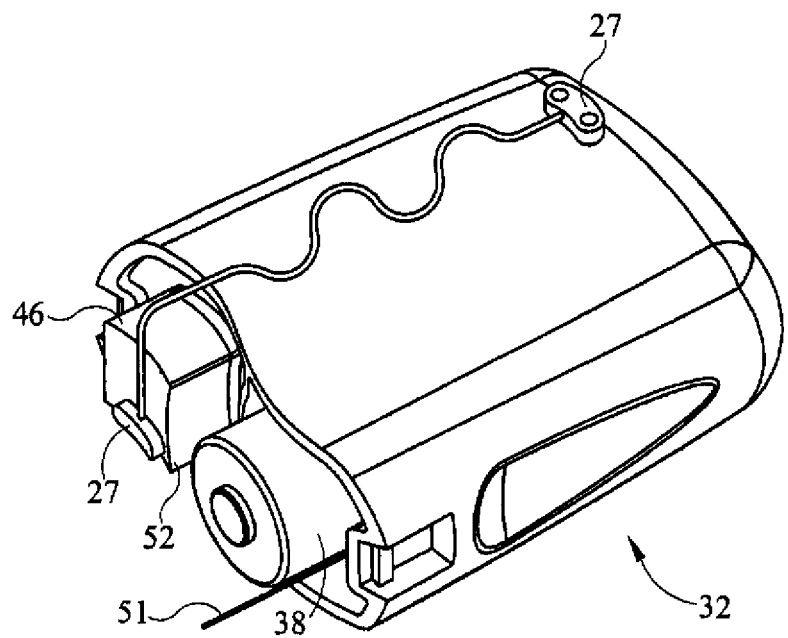
FIG. 5 is a perspective view of a replaceable unit of a volatile composition dispenser in accordance with one non-limiting embodiment.

In one non-limiting embodiment, referring to FIG. 5, when the replaceable unit 32 is not attached to the housing 12, at least one cover 27 can be positioned over the inlet orifice 56 and/or the outlet orifice 18 to at least inhibit diffusion of the volatile composition from the volatile composition container 50 to an atmosphere surrounding the volatile composition container 50. The cover 27 can comprise any suitable material that is impermeable, or at least partially impermeable, to the volatile composition or other solution or composition within the volatile composition container 50, for example. The at least one cover 27 can be removed by a user prior to the user attaching the replaceable unit 32 to the housing 12. In one non-limiting embodiment, the cover 27 can be an injection molded piece, for example, that can be attached over the various orifices using an adhesive. In various embodiments, the cover 27 may be a plug or insert that is received by the various orifices to inhibit diffusion. In other embodiments, a separate cover, such as a piece of peel away tape, for example, can be positioned over the inlet orifice 56 and/or the outlet orifice 18 to again inhibit diffusion or leakage of the volatile composition. In other various embodiments, any other suitable type of cover and/or orifice closure can be used to at least inhibit diffusion or leakage of the volatile composition from the volatile composition container 50 prior to use of the replaceable unit 32. Furthermore, if the replaceable unit 32 is attached to the housing 12 but not being actively used, at least one cover can be positioned over the outlet orifice 18 to prevent, or at least inhibit, diffusion of the volatile composition from the volatile composition container 50 of the volatile composition dispenser 10. In still other embodiments, the covers described above can be eliminated and the various orifices can be sized and shaped to at least partially inhibit diffusion or leakage of the volatile composition, for example. Of course, similar covers can be used with the volatile composition container 33, as will be recognized by those of skill in the art.

In various embodiments, the outlet orifice 18, any orifices on the volatile composition container 33, and/or optionally the inlet orifice 56, can be sized to at least inhibit molecular diffusion or leakage of the volatile composition through the orifices when the actuator 28 is not forcing the vapor phase volatile composition out of the volatile composition container 50 or the volatile composition container 33. In one non-limiting embodiment, a diameter of the various orifices can be sized in the range of about 0.1 mm to about 6 mm, alternatively about 1 mm to about 4 mm, alternatively about 1.5 mm to about 3.5 mm, and alternatively about 2 mm to about 3 mm, for example. In one non-limiting embodiment, each of the inlet orifices and outlet orifices can have a cross-sectional area in the range of about 0.008 $cm^2$ to about 0.50 $cm^2$ and, alternatively about 0.01 $cm^2$ to about 0.2 $cm^2$, for example. In one non-limiting embodiment, the inlet orifice 56 can have a length of about 0.3 mm to about 20 mm, and alternatively about 5 mm to about 10 mm. In one non-limiting embodiment, the outlet orifice 18 can have a different size than the inlet orifice 56. In various embodiments, the volatile composition dispenser 10 can have a plurality of inlet and/or outlet orifices, each with a different size, shape, geometry, and/or configuration. In other various embodiments, depending on the properties of the volatile composition being dispensed from the volatile composition dispenser 10, other orifice sizes and geometries can be used and are within the scope of the present disclosure. In further various embodiments, a plurality of orifices can be used in any suitable configuration to maximize and/or minimize the disbursement of the vapor phase volatile composition from the volatile composition container. In certain embodiments, the sizes of the orifices can be at least partially related to the speed, such as the rotational speed, for example, of the actuator 28 in order to provide a desired flow rate through the volatile composition container 50 and/or the volatile composition container 33 and a desired pressure drop within the volatile composition container 50 and/or the volatile composition container 33. Non-limiting examples of suitable air flow rates are from about 2 $cm^3$/second to about 20 $cm^3$/second or from about 5 $cm^3$/second to about 15 $cm^3$/second.

In general, when the actuator 28 is not forcing at least a portion of the vapor phase volatile composition through the outlet orifice 18, the outlet orifice 18 can be considered to be "off", or in a non-dispensing state, because of the geometry, location, configuration, and/or the size of the outlet orifice 18, which is designed to minimize evaporative losses of the volatile composition when "off". In one non-limiting embodiment, the evaporative losses though the outlet orifice 18 may never be completely eliminated, but generally may be less than about 10 mg/hour, alternatively less than about 3 mg/hour, and alternatively less than about 1 mg/hour, and alternatively less than about 0.1 mg/hour. In various embodiments, the geometry, size, and/or shape of the various orifices can be configured to yield a maximum mass flux of at least a portion of the volatile composition and a portion of the volume of air for various operating conditions of the volatile composition dispenser 10, while minimizing evaporative losses when the actuator 28 is not in an active state. This may be done, for example, by modeling the volatile composition container 50 and/or the volatile composition container 33 as a volume of ideal gas a mass flow governed by Bernoulli's equation, but modified to include a discharge coefficient. In one non-limiting embodiment, Fick's law (Eq. 1) can be used to determine orifice sizing and/or the configuration of various diffusion-limiting aspects of the volatile composition dispenser 10:

$$\dot{m} = K\left(\frac{D^2}{L}\right) \qquad \text{Eq. 1}$$

Where, K is the binary diffusion coefficient of the volatile composition, D is the orifice diameter, and L is the orifice length. The cross-sectional area of the orifice can be the primary driver of the flow rate when the actuator 28 is actively moving air through the orifice, whereas evaporation losses of the volatile composition (e.g., when the actuator 28 is in an inactive state) can be related to the cross-sectional area and the length of the orifice. Accordingly, an increase in the cross-sectional area of the orifice can impact both evaporation rates of the volatile composition and the flow rate, and an increase in the length of the orifice can mainly impact the evaporation rates of the volatile composition. While the orifice configurations have been discussed with regard to the above embodiments, those of skill in the art will understand, upon consideration of the present disclosure, that the orifice configurations can be applied to other various embodiments in a similar fashion.

In various embodiments, referring to FIGS. 4-5 and 10-16, the volatile composition container 50 can comprise the high surface area material 64. As illustrated in FIG. 4A, in some embodiments the high surface area material 64 can be contained by the volatile composition container 33. As previously discussed, in various embodiments, the high surface area material 64 can be received positioned within the volatile composition container 50. In other various embodiments, the high surface area material 64 can be positioned within the volatile composition container 33, and then the volatile composition container 33 is then received by a portion of a housing (not illustrated). The high surface area material 64 can be a porous media and/or a wick, for example, configured to maintain at least a portion of the volatile composition 49 in a liquid or a gel phase, for example. In various embodiments, the volatile composition 49 can be comprised of vaporizable materials comprising, but not limited to, solids, liquids, gels, and/or encapsulates. In other various embodiments, the volatile composition container 50 can contain a liquid volatile composition in a separate container in contact (i.e., liquid communication) with the high surface area material 64. In further various embodiments, the volatile composition container 50 can comprise a liquid volatile composition contained behind a membrane designed to allow diffusion of the liquid volatile composition through the membrane and into a vapor phase, for example. In one non-limiting embodiment, the high surface area material 64 can be comprised of any material compatible with volatile compositions, including but not limited to, cotton, cellulose, and/or other natural fibers, synthetic fibers, such as glass, polyester, nylon and/or polypropylene, sintered/fused porous glass, ceramic, and/or synthetic materials such as polyolefins. In such embodiments, voids in the high surface area material 64 can be small enough to retain the volatile compositions, yet can comprise a significant portion of the volume of the high surface area material 64 to allow for the volatile composition 49 to evaporate from the high surface area material 64 to create a vapor phase volatile composition 49'. In some instances, the voids in the high surface area material 64 can comprise more than about 50% of the total volume of the high surface area material 64. In one non-limiting embodiment, the high surface area material 64 can comprise a three dimensional shape to maximize the material's surface area and allow for maximum air flow around, and optionally through, the high surface area material 64. For vehicle applications, the high surface area material 64 can have a preferred surface area of about 1 cm$^2$ to about 100 cm$^2$ or alternatively about 5 cm$^2$ to about 50 cm$^2$, for example. The length of the high surface area material 64 can be any suitable length that fits within the volatile composition container 50 or 33. In one non-limiting embodiment, the length of the high surface area material 64 can be in the range of about 5 mm to about 10 cm, for example. In one non-limiting embodiment, the high surface area material 64 is about 10 mm by about 10 mm by about 50 mm. The three dimensional shape of the high surface area material 64 and the air gap between the high surface area material 64 and the inner wall 41 or 81 of the volatile composition container 50 or 33 can be configured to minimize a pressure drop of the volume air flow being forced through the volatile composition container 50 or 33 and can be configured to maximize the evaporative surface area of the high surface area material 64, for example.

Example configurations of the high surface area material 64 can comprise a rectangular solid, a tube, a cylinder, a channel, and/or a passage; a rectangular solid, a tube, a cylinder, a channel, and/or a passage with fins; and/or other stacks of fins similar to those used in heat exchanger designs, for example. In one non-limiting embodiment, the high surface area material 64 can be positioned adjacent to an interior wall or surface of the volatile composition container 50 or the volatile composition container 33, or, in other embodiments, the high surface area material 64 can be maintained at a distance away from an interior wall or surface of the volatile composition container 50 or the volatile composition container 33 using one or more projections, such as standoffs, pegs, posts, ribs, extensions, elongate members, and/or pins, for example. It may be desirable for there to be a gap between the high surface area material 64 and the inner wall 41 or surface of the volatile composition container 33 or 50 wherein the gap may be from about 0.5 mm to about 3 mm or alternatively from about 1 mm to about 2.5 mm. In various embodiments, the high surface area material 64 can be of sufficient size to contain a desired amount of the volatile composition 49 and, depending upon the materials selected and the configuration, the volume of the high surface area material 64 can be larger than the volume of the volatile composition 49 contained in the volatile composition container 50 or 33. In one example of a vehicle application of the volatile composition dispenser 10, the volatile composition container 50 and/or the volatile composition container 33 can have a volume of about 2 cm$^3$ to about 25 cm$^3$, and the high surface area material 64 can have a volume of about 2 cm$^3$ to about 20 cm$^3$, to contain about 1 cm$^3$ to about 10 cm$^3$ of the volatile composition. In another non-limiting example embodiment, the volatile composition container 50 or 33 can have a volume of about 2.5 cm$^3$ to about 16 cm$^3$ and the high surface area material 64 can have a void volume of about 1.5 cm$^3$ to about 12 cm$^3$, so as to contain about 1.5 ml to about 12 ml of the volatile composition 49. In one non-limiting embodiment, the volatile composition container 50 can have dimensions of about 14 mm by about 14 mm by about 54 mm.

In one non-limiting embodiment, referring to FIG. 11, the high surface area material 64 can have cross or "X" type cross-sectional configuration that can comprise a body 66, a first leg 69 extending from the body 66 in a first direction, a second leg 70 extending from the body 66 in a second direction, a third leg 72 extending from the body 66 in a third direction, and a fourth leg 74 extending from the body 66 in a fourth direction. Of course, one or more of the legs can be optional to create different cross-sectional configurations. In one non-limiting embodiment, the high surface area material 64 can have a first dimension 76 of about 2 mm to about 5 mm and a second dimension 78 of about 5 mm to about 8 mm, for example. In various embodiments, the cross-sectional configuration of the high surface area material 64 can be generally "I" shaped (FIG. 12), circular (FIG. 13), star shaped, or can comprise fins 63 or other extensions (FIG. 14), for example. Such embodiments, can increase the surface area of the material 64, while still providing a space for the vapor phase composition to evaporate into. Of course, any other suitable cross-sectional configuration can be used with and is within the scope of the present disclosure. In various embodiments, the cross-sectional area of the high surface area material 64 may vary throughout the length, or other dimension, of the high surface area material 64. In one non-limiting embodiment, a first high surface area material and at least a second high surface area material can be positioned within the volatile composition container 50 or 33, for example. The first material and at least the second material can be stacked on top of each other and separated by a gap, or can be placed end to end in the volatile composition container 50 or 33, for example. In certain embodiments, the volatile composition container 50 or 33 and/or the high surface area material 64 can comprise at least one baffle or other air flow devices configured to direct the air flow through the volatile composition container 50 or 33.

Figure 15:
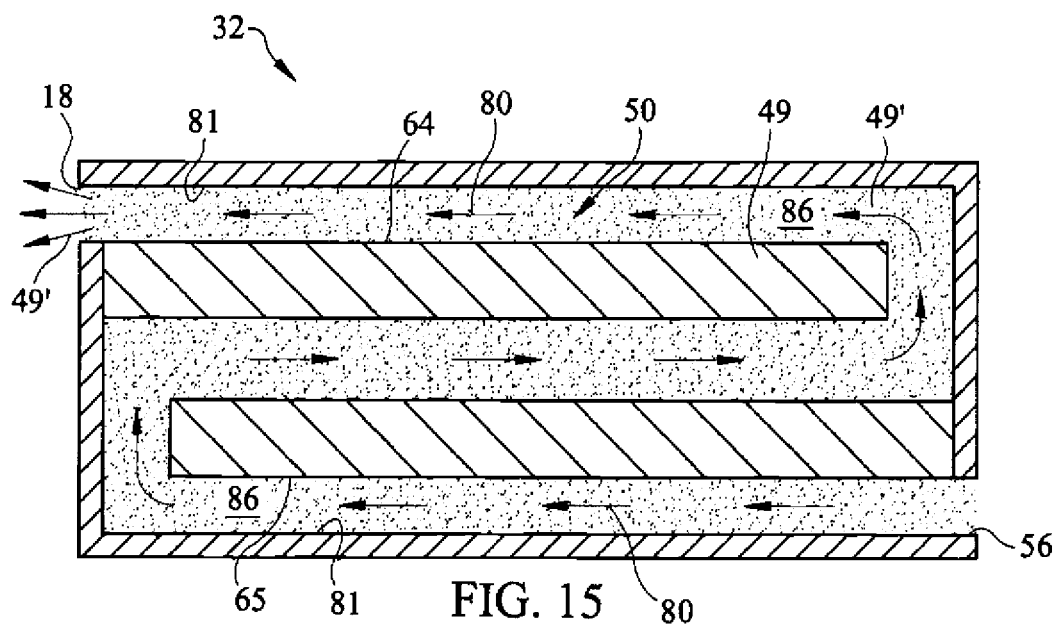
FIG. 15 is an example cross-sectional view of a volatile composition container having a material positioned therein in accordance with one non-limiting embodiment.
Figure 16:
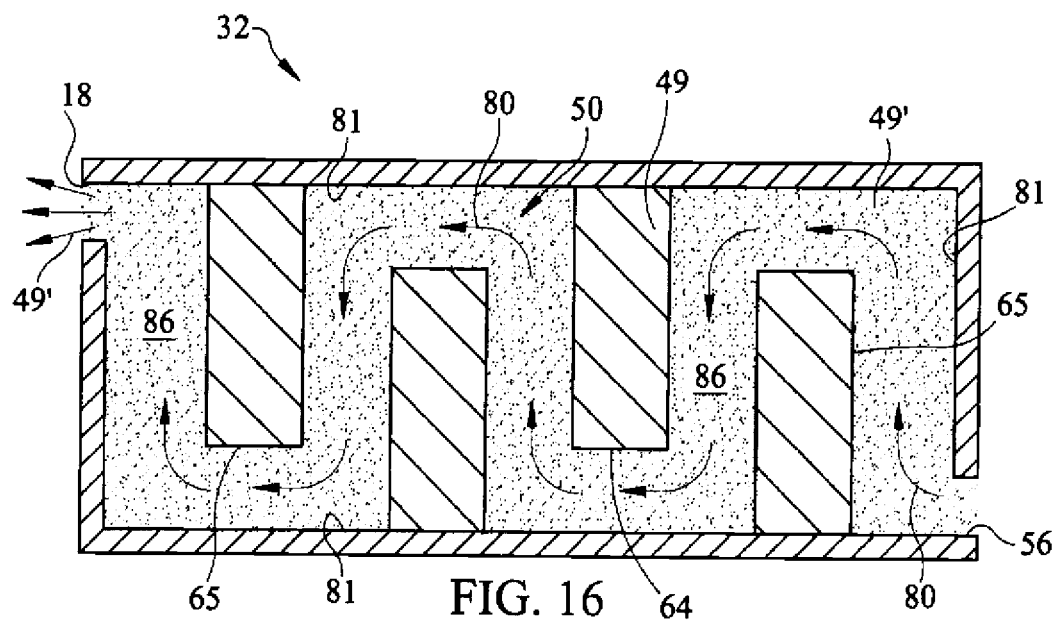
FIG. 16 is another example cross-sectional view of a volatile composition container having a material positioned therein in accordance with one non-limiting embodiment.

In one non-limiting embodiment, referring to FIGS. 15 and 16, the high surface area material 64 can be configured to provide a tortuous flow path (indicated by arrows 80) for the volume of air passing into the inlet orifice 56 and out of the outlet orifice 18 through a space 86. The space 86 can be defined proximate to a surface 65 of the high surface area material 64 and/or intermediate a surface of the high surface area material 64 and a surface or inner wall 81 of the volatile composition container 50 or 33. In various embodiments, the flow path of the volume of air being forced or passed through the volatile composition container 50 or 33 can traverse, pass along, and/or pass over at least a portion of the surfaces of the high surface area material 64 containing a volatile composition 49. In other embodiments, the flow path of the volume of air can move in a direction parallel to, or substantially parallel to, at least a portion of the surfaces of the high surface area material 64, for example. In various embodiments, the flow path 80 can be directed through the high surface area material 64. Such flow paths can allow the volume of air to force the vapor phase volatile composition 49' out of the volatile composition container 50 or 33 when the actuator provides the volume of air to the inlet 56.

As some volatile compositions tend to evaporate into a vapor phase to achieve a more equilibrium state, the high surface area material 64 can be configured at least inhibit this evaporation and at least partially maintain a portion of the volatile composition 49 in a liquid phase, a semi-liquid phase, and/or a gel phase, to at least inhibit evaporation of the volatile composition and thereby at least inhibit diffusion of the vapor phase volatile composition 49' from the volatile composition container 50 and/or the volatile composition container 33 prior to the desired dispensing time. Additionally, the high surface area material 64 can at least inhibit leakage of the liquid volatile composition 49 from the volatile composition container 50 or 33. In various embodiments, as the volatile composition 49 transforms into its vapor phase over a period of time, the volume of the high surface area material 64 can be reduced, thereby providing more space in the volatile composition container 50 or 33 to receive the vapor phase volatile composition 49'. In one non-limiting embodiment, as the volume of air from the actuator 28 enters the volatile composition container 50 through the inlet 56, the volume of air can mix with the vapor phase volatile composition 49' to cause a portion of the vapor phase volatile composition 49' to be ejected though the outlet orifice 18 and into the atmosphere of the vehicle, for example. In various embodiments, the outlet orifice 18 can be in fluid communication with the space 86 within the volatile composition container 50 comprising the vapor phase volatile composition. In still other various embodiments, the space 86 can be defined proximate to a surface 65 of the high surface area material 64 and/or intermediate the surface 65 of the high surface area material and a surface or inner wall of the volatile composition container 33, depending on whether the volatile composition container 33 is provided in a particular embodiment. In one non-limiting embodiment, the outlet orifice 18 can be located on a top portion and/or a side portion of the volatile composition container 50 and in some embodiments a plurality of outlet orifices 18 can be provided. Any other suitable configurations of the outlet orifice 18, the high surface area material 64, and/or the space 86 can be provided within the volatile composition container 50 or 33.

Figure 10:
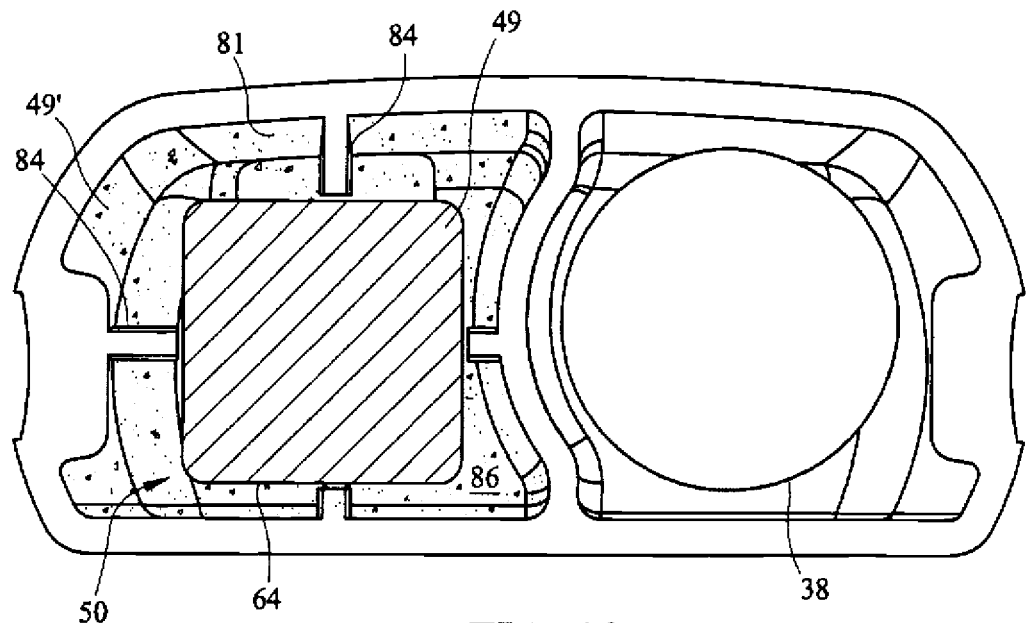
FIG. 10 is a cross-sectional view taken along line 10-10 of FIG. 3 in accordance with one non-limiting embodiment.

In one non-limiting embodiment, referring to FIG. 10, the volatile composition container 50 can comprise one or more projections 84 extending into the volatile composition container 50 from the inner wall 81 or surface of the volatile composition container 50. The one or more projections 84 can engage a portion of the high surface area material 64 in order to maintain the high surface area material 64 at a distance away from the inner wall 81 of the volatile composition container 50. In one non-limiting embodiment, the high surface area material 64 can comprise one or more slots (not illustrated) for receiving the one or more projections 84 to aid in the positioning and securing of the high surface area material 64 within the volatile composition container 50. In one non-limiting embodiment, the high surface area material 64 comprises projections that are configured to engage inner wall 81. By maintaining the position of the high surface area material 64 at a distance away from the inner wall 81, a space 86 formed intermediate the inner wall 81 and the high surface area material 64 can become saturated, or at least partially saturated, with the vapor phase volatile composition 49', as the liquid volatile composition 49 within high surface area material 64 evaporates. In various embodiments, the one or more projections 84 can extend lengthwise about the inner wall 81 of the volatile composition container 50, while in other various embodiments, the one or more projections 84 can extend crosswise across the inner wall 81 of the volatile composition container 50. In other embodiments, the one or more projections can be positioned on the inner wall 81 in any other suitable configuration. As will be appreciated by those of skill in the art, after consideration of the present disclosure, various configurations of the high surface area material 64 may not require the use of one or more projections 84. In various embodiments, the one or more projections 84 can serve as baffles to direct the flow of the volume of air. Furthermore, in various embodiments, the one or more projections 84 can comprise pegs, ribs, posts, standoffs, elongate members, and/or pins, for example, which can serve to position the high surface area material 64 within the volatile composition container 50. In still other various embodiments, the high surface area material 64 can comprise features extending from the high surface area material 64 that enable a surface of the high surface area material 64 to be maintained at a distance away from the inner wall 81 of the volatile composition container 50. Such features of the high surface area material 64 can be used independent of or in conjunction with the one or more projections 84.

Figure 10A:
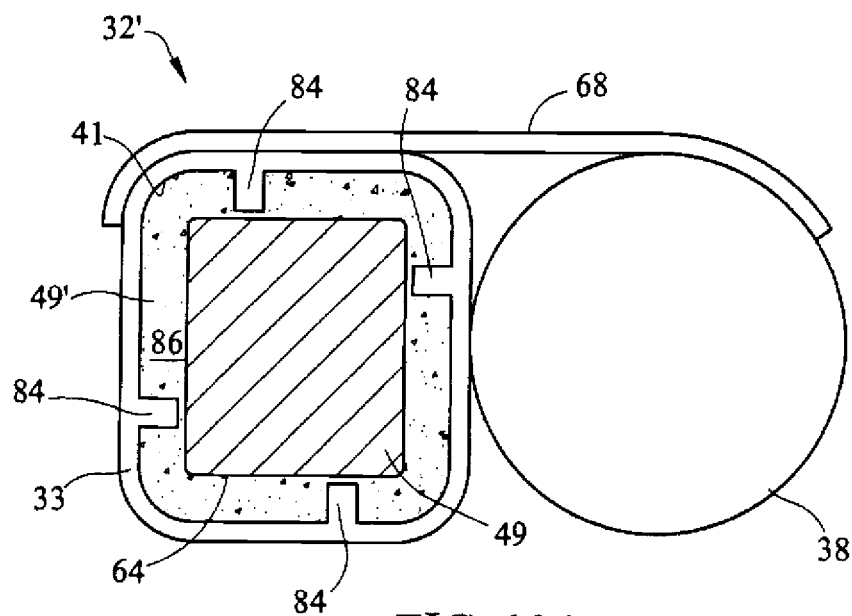
FIG. 10A is a cross-sectional view taken along line 10A-10A of FIG. 4A in accordance with one non-limiting embodiment.

In various embodiments, as illustrated in FIG. 10A, the volatile composition container 33 can also comprise one or more projections 84 used to position the high surface material 64 within the volatile composition container 33. Such projections 84 can extend from the inner wall 41 of the volatile composition container 33 and engage a portion of the high surface area material 64 to maintain the portion of the high surface area material 64 at a distance away from the inner wall 41. This positioning can allow a space 86 to be created between the inner wall 41 of the volatile composition container 33 and the high surface material 64 containing the volatile composition 49'. The space 86 can be configured to receive a vapor phase volatile composition 49' upon evaporation of the volatile composition 49. Similar to that discussed above with reference to FIG. 10, the high surface area material 64 within the volatile composition container 33 can also comprise features that enable a surface of the high surface area material 64 to be maintained at a distance away from the inner wall 41 of the volatile composition container 33. In other various embodiments, depending on the configuration of the high surface area material, such as the example high surface area material configurations of FIGS. 11 and 12, the one or more projections 84 can be optional. In still other various embodiments, again dependent on the configuration of the high surface material, any suitable number of projections 84 can be used. As will be appreciated by one skilled in the art after consideration of the present disclosure some types of configurations of the high surface area material 64, such as an "X" type cross-sectional configuration, may not require the use of projections within the container 50 or 33. With an "X" type cross-sectional configuration (FIG. 11), for example, the legs 69, 70, 72, and 74 may each engage the inner wall 81 of the container 50 or 33 to maintain the positioning of the high surface area material 64 while allowing for proper air flow through the container 50 or 33.

In various embodiments, referring to FIGS. 2, 6, and 7, the actuator 28 can comprise any suitable actuator or components configured to produce and/or intermittently move a volume of air through the volatile composition container 50 and/or portions of the volatile composition dispenser 10. In one non-limiting embodiment, the actuator 28 can comprise a fan assembly 100 comprising a motor 102. The motor 102 can comprise a drive shaft 101. The actuator 28 can be configured to produce and intermittently move the volume of air and provide the same to the inlet orifice 56 of the volatile composition container 50. In various embodiments, an actuator outlet 104 of the actuator 28 can be positioned proximate to the inlet orifice 56 of the volatile composition container 50 to place the actuator outlet 104 and the inlet orifice 56 in fluid communication. In one non-limiting embodiment, an intermediate structure can be positioned between the inlet orifice 56 and the actuator outlet 104, such as a bulkhead 110, for example. The bulkhead 110 can define a bulkhead orifice 112 configured to allow the volume of air to travel from the actuator outlet 104 to the inlet orifice 56. The bulkhead 110 can be configured to protect or isolate the various internal components of the housing 12 when the replaceable unit 32 is not attached. The orifices 104, 112, and 56 can be designed to minimize pressure and/or flow losses, for example. In various embodiments, a one-way valve can be positioned intermediate the actuator outlet 104 and the inlet orifice 56 to regulate the flow of the volume of air into the volatile composition container 50. In various embodiments, a one-way valve can be positioned intermediate the outlet orifice 18 and the atmosphere outside the volatile composition dispenser 10 to regulate the flow of the volume of air and the vapor phase volatile composition 49' out of the volatile composition container 50. As will be appreciated by those of skill in the art, after consideration of the present disclosure, if a one-way valve is used proximate to the inlet orifice 56 and/or outlet orifice 18, in various embodiments, the length of these orifices may be reduced and/or the cross sectional area of the inlet orifice and/or outlet orifice may be increased.

Further to the above, in various embodiments, referring to FIGS. 6 and 7, the fan assembly 100 can comprise a fan housing 114, a fan housing cover 116, a rotatable hub 118, and at least two fan blades 120 extending from the rotatable hub 118 or otherwise attached to or formed with the rotatable hub. In one non-limiting embodiment, the diameter of the rotatable hub 118 can be about 8 mm to about 20 mm, for example. The fan assembly 100 can define a fan inlet 124. The drive shaft 101 can be operably engaged with the rotatable hub 118 such that rotation of the drive shaft 101 by the motor 102 rotates the rotatable hub 118 and thereby rotates the at least two fan blades 120. In one non-limiting embodiment, the fan assembly 100 can be a centrifugal (i.e., radial) fan. Each blade 120 can comprise an air forcing surface 122 that is positioned in a direction parallel to, or substantially parallel to, an axis of rotation of the rotatable hub 118 (illustrated as axis "A".) In one non-limiting embodiment, an electrical current can be provided to the motor 102 via electrically conductive leads or terminal (not illustrated) to rotate the rotatable hub 118 in a direction indicated by arrow 126. Such rotation can cause a volume of air to be drawn into the fan housing 114 through the fan inlet 124. With a centrifugal fan configuration, the air flowing through the fan assembly 100 can be drawn through the fan inlet 124 and forced in a radial direction relative to the drive shaft 101. In other embodiments, the volume of air can be drawn from the atmosphere outside of the volatile composition dispenser 10 through any suitable passageway, such as at the interface between the top shell 15 and the bottom shell 17 or through an orifice on the housing 12, for example. The rotation of the at least two fan blades 120 can force the volume of air out of the fan housing 114 through the actuator outlet 104 and into the inlet orifice 56 of the volatile composition container 50. In various embodiments, the at least two fan blades 120 can be arcuate (as illustrated), straight, and/or can have curved, straight, and/or arcuate portions. Additionally, the at least two fan blades 120 can have various cross-sectional shapes, such as an airfoil shape or a tapered shape, for example. As will be appreciated by those of skill in the art, after consideration of the present disclosure, a centrifugal fan can provide high efficiency with relatively small dimensions, and changes in pressure may have little influence on pressure head drops through the volatile composition container 50. In various non-limiting embodiments, the fan may produce pressures in the range of about 3 Pascals to about 20 Pascals or alternatively from about 5 Pascals to about 15 Pascals.

In one non-limiting embodiment, the motor 102 can be a Mabuchi RF-J20WA-5Z145 motor that rotates the drive shaft 101 at about 6200 revolutions per minute when 0.7 VDC is supplied to the motor 102 from the power source 38 and rotates the driveshaft 104 at about 9400 revolutions per minute when 1.0 VDC is supplied to the motor 102 from the power source 38. In various embodiments, the flow rate of the volume of air generated by the motor 102 can be in the range of about 1.0 to about 8.0 mL/sec at about 0.7 VDC to about 6.0 to about 16.0 mL/sec at 1.0 VDC, depending upon the cross sectional area of the inlet orifice 56 and the outlet orifice 18. By supplying various voltage levels to the motor 102, the rotational speed of the drive shaft 101 and the resultant flow rate of the volume of air can be varied. Any other suitable motor can also be used with the fan assembly 100, such as a Sunon UB393-10 fan assembly, for example. Additionally, the controller 30 can supply the motor 102 with voltage using any suitable technique known to those of skill in the art. In various embodiments, a pulse width modulation technique can be used to provide voltage to the motor 102 over a specified range, such as about 0.7 VDC to about 1.0 VDC, for example. Additional circuitry or components, such as an analog-to-digital converter, can be used to compensate for various factors, such as the power source voltage and the ambient temperature, for example. In order to isolate or limit vibration due to the rotation of the drive shaft 101 and/or the rotatable hub 118, vibration suppression devices or techniques can be used, such as silicon or thermoplastic elastomeric fan supports, for example, and/or the use of a gasket at the interface of the replaceable unit 32 and the housing 12.

In various embodiments, the controller 30 can be positioned in electrical communication with the actuator 28, such that the controller 30 can instruct the actuator 28 when to activate and which speed to rotate in order to force the volume of air through the volatile composition container 50. In one non-limiting embodiment, the controller 30 can be any suitable type of controller, such as a microcontroller, for example. In one non-limiting embodiment, the controller 30 can be a Texas Instruments MSP430F2132 controller, for example. In various embodiments, the controller 30 can comprise one or more user input buttons or switches 26 configured to provide an input signal to the controller 30 when depressed by a user, such that the controller 30 can send corresponding output signals to the actuator 28 and/or the user feedback module 16, for example. In one non-limiting embodiment, the various user input buttons or switches 26 can comprise a power on/off switch configured to power on or power off the volatile composition dispenser 10 and at least one volatile composition dose amount button configured to allow the user to adjust the amount of volatile composition dispensed by the volatile composition dispenser 10. As will be appreciated, the input buttons or switches 26 can be any combination of buttons and/or switches, such as push buttons, sliders, dials, knobs, for example. In various embodiments, the amount of the volatile composition dispensed over a predetermined time interval can be controlled by adjusting the rate at which the actuator 28 is activated by the controller 30 (i.e., by adjusting the time period the actuator 28 is active and the time period the actuator 28 is inactive), by adjusting the speed at which the air is moved when the actuator 28 is active (i.e., by adjusting the rotational speed by adjusting the voltage to the motor 102), and/or by a combination of both techniques. In one non-limiting embodiment, the volatile composition dispenser 10 can have a "boost" button for delivering a dose of the volatile composition to the atmosphere of the vehicle on demand. For example, if the boost button is depressed or otherwise activated, the actuator 28 can be activated for a specified time period, such as 30 to 60 seconds or at a specified rotational speed, for example.

In various embodiments, the controller 30 can also be in electrical communication with a temperature sensor configured to sense the temperature within the interior atmosphere of the vehicle, for example, and a motion sensor configured to determine whether the vehicle is in motion. In various embodiments, the temperature sensor can send a signal to the controller 30 indicative of the temperature of the vehicle, such that the controller 30 can provide an output signal to the actuator 28, or other various components of the volatile composition dispenser 10, indicative of a volatile composition dosing amount for a particular temperature and/or temperature range. For example, higher temperature ranges may require greater dose amounts than lower temperature ranges to achieve the desired result. In one non-limiting embodiment, the motion detector can send a signal to the controller 30 indicative of whether the vehicle is in motion, such that the controller 30 can adjust the volatile composition dosing amount appropriately by instructing the actuator 28 accordingly. If the vehicle is not in motion, the volatile composition dosing amount can be reduced or, in other various embodiments, the volatile composition dispenser 10 can remain inactive, for example. As a result, the volatile composition dispenser 10 can be power efficient such that it can maximize the life of the power source 38, for example. In various embodiments, if the vehicle is moving, the appropriate volatile composition dosing amount can continue to be dispensed in an intermittent or periodic fashion to inhibit user acclimation to the volatile composition. In such an embodiment, the volatile composition dispenser 10 can be activated for 1-30 seconds, for example, and then be inactive for 10-200 seconds, for example. In other various embodiments, the volatile composition dispenser 10 can be set by a user to provide a desired intermittent dosing amount.

In various embodiments, the controller 30 can also be in communication with an air flow sensor, a volatile composition concentration sensor, and/or a timer. In one non-limiting embodiment, the air flow sensor can be configured to determine the air flow rate within the interior atmosphere of the vehicle. In such an embodiment, the air flow sensor can send a signal indicative of the air flow rate to the controller 30, such that the controller can provide a volatile composition dosing instruction to the actuator 28 corresponding to the air flow rate within the atmosphere of the vehicle. The air flow sensor can also be used to detect the air circulation within the interior atmosphere of the vehicle and/or whether one or more windows are down, for example, to determine how many air exchanges are taking place in the interior atmosphere of the vehicle over a particular interval of time. This information can then be correlated to a volatile composition dosing amount. In various embodiments, the concentration sensor can sense the concentration of the volatile composition within the interior atmosphere of the vehicle. Similar to the air flow sensor, the concentration sensor can send a signal indicative of the concentration of the volatile composition in the interior atmosphere of the vehicle to the controller 30, such that the controller 30 can adjust the volatile composition dosing amount according to the concentration of the atmosphere of the vehicle. In various embodiments, the timer can be configured to send a signal to the controller 30, after a predetermined time interval, to indicate to the controller 30 that a volatile composition dose needs to be provided by the dispenser 10. In various embodiments, at least two of the air flow sensor, the temperature sensor, the motion sensor, the concentration sensor, and the timer can be used in conjunction with each other to instruct the volatile composition dispenser 10 to dispense an appropriate volatile composition dose amount to the interior atmosphere of the vehicle, for example. In one non-limiting embodiment, the volatile composition dispenser 10 can also comprise a volatile composition sensor configured to sense information regarding the amount and type of the volatile composition 49 within volatile composition dispenser 10 and relay the same information to the controller 30 for processing.

In various embodiments, the control technique or approach for the actuator 28 can be at least based on characteristics of the high surface are material 64, the volatile composition, and/or the volatile composition container 50. In various embodiments, the control technique or approach for the actuator 28 can be at least based on characteristics of the volatile composition container 33. Volatile compositions with lower vapor pressures will likely evaporate slower than volatile compositions with higher vapor pressures. In various embodiments, the actuator 28 may not be activated until the space 86 within the volatile composition container 50 has reached full saturation or near full saturation of vapor phase volatile composition 49'. In one non-limiting embodiment, the deactivation time period of the actuator 28 can be related to the time period necessary for the volatile composition 49 to evaporate and saturate, or at least partially saturate, the space 86 with the vapor phase volatile composition 49'. In one non-limiting embodiment, the activation time period of the actuator 28 can be related to the time period necessary to expel substantially all of the vapor phase volatile composition 49' from the of the volatile composition container 50 into the atmosphere of the vehicle. Once the vapor has been expelled from the volatile composition container 50, the actuator 28 can be placed in an inactive state to again allow a portion of the volatile composition 49 to enter the vapor phase. As will be appreciated by those of skill in the art, for a particular volatile composition, volatile composition containers with a relatively greater volume of the space 86 may require a longer time period to achieve the desired saturation levels, while volatile composition containers with a relatively lesser volume of the space 86 may require a shorter time period to achieve the desired saturation levels. Furthermore, as the level of the volatile compound 49 and/or the size of the high surface area material 64 decreases over time, the time period necessary for saturation, or partial saturation, may increase. The controller 30 can factor these characterizations when determining the various control techniques for the actuator 28. In one non-limiting embodiment, the time period required to achieve vapor phase volatile composition saturation can be less than about 5 seconds, for example. Formulations with higher vapor pressures may evaporate into a vapor phase at a faster rate than formulations with lower vapor pressures. Therefore, formulations with higher vapor pressures may reach equilibrium faster than formulations with lower vapor pressures.

By activating the actuator 28 for a period of time equal to, or approximately equal to, the amount to time necessary to expel at least most of the vapor phase volatile composition 49', the lifetime of the power source 38 can be optimized. Through control of the actuator 28, maximum vapor phase volatile composition 49' release can be achieved with a minimum amount of actuator running time. In various embodiments, the sequencing or pattern of activator actuation, or the flow rate of the volume of air produced by the actuator 28, can be adjusted to allow full or near full saturation of the volatile composition within the space for maximizing the vapor phase volatile composition release. In one non-limiting embodiment, the actuator 28 can be activated for about 1-10 seconds and then deactivated for about 1-10 seconds, for example.

In various embodiments, the duration of activation of the actuator 28 or the flow rate of the volume of air provided by the actuator 28 can be increased to provide a higher intensity of volatile composition expulsion from the volatile composition dispenser 10. The actuator 28 can be actuated for about 10-60 seconds and then deactivated for about 10-300 seconds, for example. By providing a period of time between consecutive activations of the actuator 28, a user is more likely to notice a scent of the volatile composition 49 again and hence avoid habituation. The use of the higher intensity expulsion also, in various embodiments, allows the volatile organic compositions (VOCs) present in the vehicle, and other background volatiles, such as malodors, for example, to be at least partially overcome. In one non-limiting embodiment, a typical vehicle may have VOCs that range between 10 and 1000 parts/per/billion. Some newer vehicle may have VOCs that are in the parts/per/million level. As may be appreciated by those skilled in the art, the level of VOCs present in the vehicle may be dependent on a number of factors, such as ambient temperature, for example. In some circumstances, VOCs in the atmosphere of a vehicle may interfere with the sensorial detection of fragrances released into the air by the human nose. Accordingly, pulsing a higher level of the vapor phase volatile composition 49' into the atmosphere of the vehicle may allow a user to more strongly detect the vapor phase volatile composition 49'. In one non-limiting embodiment, actuating the actuator 28 for 10-60 seconds can allow the vapor phase volatile composition 49' to be more noticeable and providing a delay of about 10-300 seconds can allow the concentration to drop, allowing the user or passenger to more strongly notice the next expulsion. As will be appreciated by those of skill in the art, different pulsing frequencies and/or different air flow rates can be used to deliver different scent experiences, for example.

Table 2 provides example non-limiting activation patterns of the actuator 28.

TABLE 2

| Example Duty Cycles | Actuator Inactive Time Period | Actuator Active Time Period |
|---|---|---|
| High (50% duty cycle) (may be more efficient for volatile composition release but may use more power due to frequent activation and deactivation of the actuator) | 1 sec | 1 sec |
| High (50% duty cycle) (may be less efficient for volatile composition release but may not use as much power due to activation and deactivation of the actuator) | 10 sec | 10 sec |
| High (50% duty cycle) (may be less efficient for volatile composition release but may create a stronger pulse of fragrance to drive more volatile composition noticeably into the atmosphere of the vehicle with a larger gap between pulses to deprive the scent and then provide the scent again) | 30 sec | 30 sec |
| Medium (25% duty cycle) | 3 sec | 1 sec |
| Medium (33% duty cycle) | 40 sec | 20 sec |
| Low (10% duty cycle) | 90 sec | 10 sec |
| Low (10% duty cycle) | 9 sec | 1 sec |
| Very Low (5% duty cycle) | 190 sec | 10 sec |
| Very Low (5% duty cycle) | 95 sec | 5 sec |

In various embodiments, the release rate of a volatile composition 50 from the volatile composition dispenser 10 can be about 0.5-12 mg/hour, alternatively about 1.0-8.0 mg/hour, or alternatively about 2.0-4.0 mg/hour for example. In one non-limiting embodiment, a high surface area material 64 having dimensions of about 10 mm×10 mm×50 mm is contained within the volatile composition container 50 or 33. In this embodiment, the high surface area material 64 is an absorbent polyolefin fiber, available from Filtrona Porous Technologies (D4507B). As may be appreciated, however, other suitable materials may be used. In this embodiment, the high surface area material 64 is loaded with 4 grams of a volatile composition 49, such as Benzyl Aceatate, for example. In this embodiment, the volatile composition 49 has a vapor pressure of 190 Pa at 20° C. As may be appreciated, other volatile compositions may have a variety of vapor pressures. In this embodiment, with inlet and outlet orifice dimensions of 2.5 mm diameter and 10 mm long, the release rate of the volatile composition 49 from the volatile composition dispenser 10 is about 3.5 mg/hour when the actuator 28 runs at a 20% duty cycle (30 seconds on/120 seconds off) at 0.7 VDC at an ambient temperature of 70° F. In such an embodiment, the air flow rate through the volatile composition container 50 may be about 5.5 $cm^3$/sec. In one non-limiting embodiment, the release rate of the volatile composition 49 from the volatile composition dispenser 10 is about 5 mg/hour when the actuator 28 runs at a 20% duty cycle (30 seconds on/120 seconds off) at 1.0 VDC at an ambient temperature of 70° F. In such an embodiment, the air flow rate through the volatile composition container 50 may be about 12 cc/sec. Comparatively, the release rate of the volatile composition 49 may be about 16 mg/hour and about 24 mg/hour when the actuator 28 runs at a 100% duty cycle at 0.7 VDC and 1.0 VDC, respectively, at an ambient temperature of 70° F. While an operation duty cycle of 100% for an extended period of time may decrease the level of the power in the power source 38, in various embodiments, the actuator may operate at a high duty cycle, such as 100%, for a relatively short period of time, such as less than about 30 seconds, or less than about 10 seconds. In these embodiments, such operation (i.e., a "boost" operation), can be used to temporarily increase the release rate of the volatile composition dispenser 10 to overcome a malodor or overcome the lack of fragrance noticeably, which may be caused, in part, by the presence of VOC's as described previously.

In various embodiments, the volatile composition dispenser 10 can comprise a user feedback module 16 configured to provide feedback to the user regarding the status of the volatile composition dispenser 10. In one non-limiting embodiment, the user feedback module 16 can be used to alert the user of a property of the volatile composition dispenser 10. In such embodiments, the feedback can be visual and/or audible and can indicate to the user, among other things, whether the volatile composition dispenser 10 is powered on, what volatile composition dosing amount is being dispensed, the power level of the power source 38, the amount, type, or level of the volatile composition 49 within the volatile composition container 50, and/or any other suitable feedback helpful or beneficial to the user. In various embodiments, referring to FIGS. 1 and 2, the user feedback module 16 can comprise one or more one indicators 42, such as a plurality of light sources, for example, electrically coupled to the controller 30 and/or to the power source 38, and a translucent portion 43 in the housing 12, such that the one or more indicators 42 can be viewed by the user though the housing 12. In one non-limiting embodiment, the one or more indicators 42 can be oriented in any suitable fashion such that various lights of the one or more indicators 42 can emit visible light through the translucent portion 43 of the housing 12, depending on what type of feedback is being provided to the user. In one non-limiting embodiment, the translucent portion 43 of the housing 12 can comprise any suitable shape and the one or more indicators 42 can be arranged in a similar shape so that as one indicator, such as a light source, for example, is powered or unpowered, the user is provided with a first feedback and, as two or more light sources are powered or unpowered, the user is provided with at least a second feedback and so forth. In one non-limiting embodiment, at least one button 26 is at least partially translucent allowing for one or more indicators 42 to be viewable through the button 26.

In various embodiments, the replaceable unit 32 can comprise any number of containers, each container comprising a different, slightly different, or the same volatile composition. In other various embodiments, the replaceable unit 32 can comprise multiple chambers therein, each chamber comprising a different, slightly different, or the same volatile composition, for example. In one non-limiting embodiment, each volatile composition can comprise a different, slightly different, or the same vapor pressure range, for example. This feature can be useful when a user wants to dispense a first dose amount of a first volatile composition and a second dose amount of a second volatile composition, for example. In an instance in which more than one volatile compound is within one container or chamber of a container, the volatile composition with the higher vapor pressure range may transform from a liquid phase, a semi-liquid, and/or a gel phase into a vapor phase prior to the volatile composition with the lower vapor pressure range transforming into a vapor phase. In this circumstance, the volatile composition with the higher vapor pressure range would likely be dispensed first, while the volatile composition with the lower vapor pressure range would likely be dispensed second. In various embodiments, where different volatile compositions with different vapor pressure ranges are in separate containers or chambers, the different volatile compositions can be dispensed from their respective containers simultaneously, for example. As a result, various volatile compositions can be dispensed from the volatile composition dispenser 10 to create a mixture of scents, for example, if the volatile composition is a fragrance.

Figure 17:
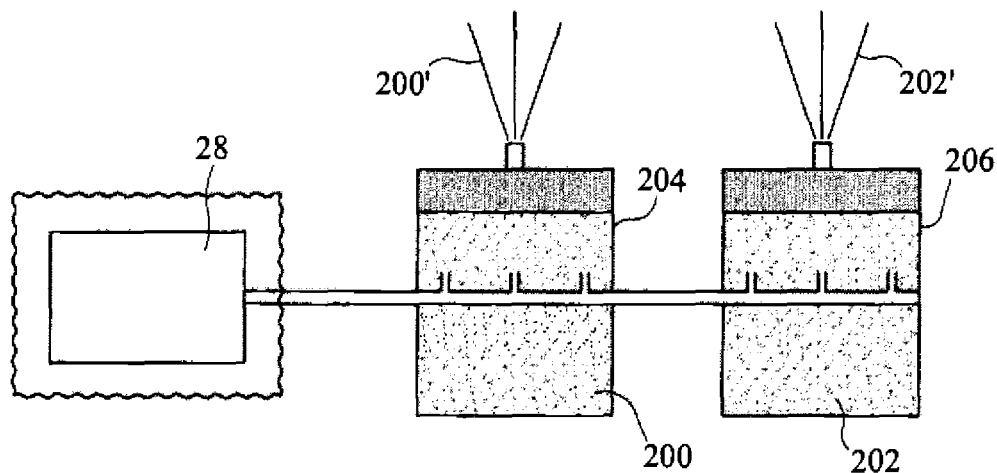
FIG. 17 is a schematic illustration of an actuator and volatile composition container configuration in accordance with one non-limiting embodiment.
Figure 18:
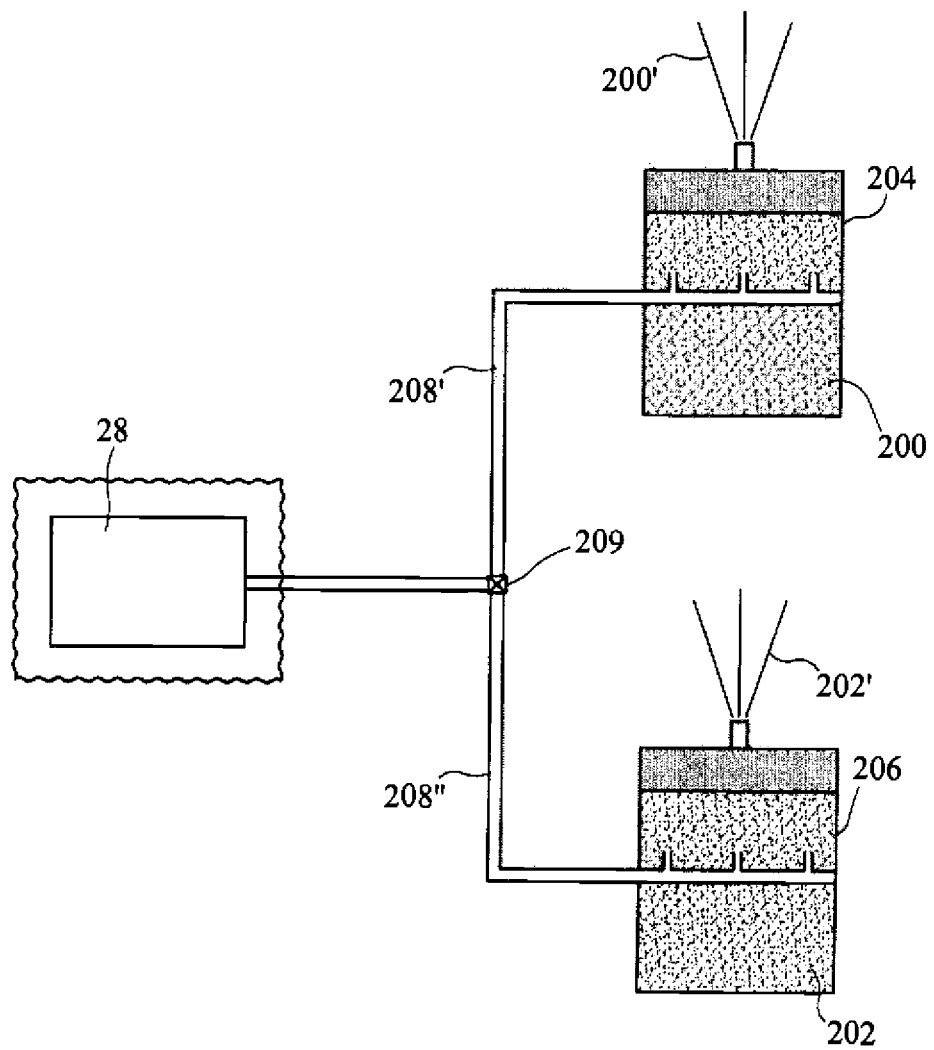
FIG. 18 is a schematic illustration of another actuator and volatile composition container configuration in accordance with one non-limiting embodiment.

Further to the above, in various embodiments, the multiple volatile composition containers can be positioned in series, in parallel, and/or in any other suitable configuration. In one non-limiting embodiment, referring to FIG. 17, where the multiple volatile composition containers are positioned in series, the volume of air from the actuator 28 can enter a first container 204. The container 204 may contain a first volatile composition 200 and dispense a vapor phase of first volatile composition 200' from the first container 204. A portion of the volume of air can then enter a second container 206 containing a second volatile composition 202 and dispense a vapor phase of second volatile composition 202' from the second container 206, for example. In various embodiments, referring to FIG. 18, when the multiple volatile composition containers are positioned in parallel, the volume of air can be split between a first passageway 208' leading to the first container 204' and a second passageway 208" leading to the second container 206. In such a configuration, the first and second containers 204 and 206 can be configured to simultaneously provide a volatile composition dose of the vapor phase of the volatile composition 200' and 202', respectively, for example. In various embodiments, a selectable switch and/or a valve 209 can be used to direct the volume of air into one, or some, of the containers instead of other containers to allow a user the ability to configure the volatile composition dispenser 10 to provide a particular volatile composition dose or a combination of volatile composition doses for a particular situation. Stated another way, the user could dose a first volatile composition 200, or fragrance, in a first situation and, dose a second volatile composition 202, or fragrance, in a second situation, for example. In various embodiments, the selectable valve 209 can be controlled by a member, a button, and/or a switch on the housing 12, for example. FIGS. 17 and 18 are merely for illustrative purposes, in that ideally the flow paths from the actuator 28 to the containers 204 and 206 are short in length and relatively large in diameter to minimize flow and pressure losses.

Figure 19:
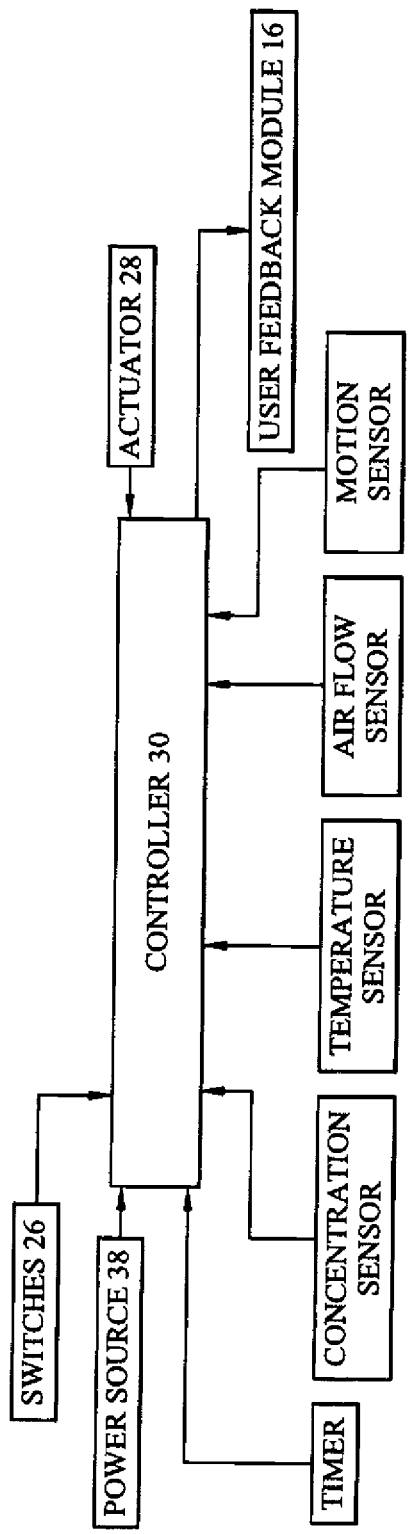
FIG. 19 is a flow chart describing an electrical and sensing system of a volatile composition dispenser in accordance with one non-limiting embodiment.

In various embodiments, FIG. 19 illustrates a circuit diagram for the volatile composition dispenser 10. In one non-limiting embodiment, the power source 38 can provide power to the controller 30. In such an embodiment, the power source 38 can also provide an electrical signal to the controller 30 indicative of a power level of the power source 38, for example. In various embodiments, a temperature sensor, an air flow sensor, a concentration sensor, a motion sensor, and a timer, for example, can be in electrical communication with the controller 30 such that each sensor can send various signals to the controller 30 indicative of the temperature of the interior atmosphere of the vehicle, the air flow within the interior atmosphere of the vehicle, the volatile composition concentration within the interior atmosphere of the vehicle, whether the vehicle is in motion, and/or the time lapse since the last dose of the volatile composition was provided by the volatile composition dispenser 10 to the interior atmosphere of the vehicle. In one non-limiting embodiment, the controller 30 can then interpret the signals received from the various sensors and can instruct the actuator 28 and optionally the user feedback module 16 accordingly. In such an embodiment, the user feedback module 16 can be in electrical communication with the controller 30 and can be configured to receive an output indicative of various properties of the vehicle sensed by the sensors and/or provided by the power source 38, for example. In various embodiments, the actuator 28 can be in electrical communication with the controller 30 to receive electrical power and/or intermittent electrical power from the controller 30. In one non-limiting embodiment, the switches 26 can also be in electrical communication with the controller 30 such that when the user depresses or activates one or more switches 26, a signal can be sent to the controller 30 indicative of the user's input. Those of skill in the art, upon consideration of the present disclosure, will understand that this circuit is merely an example configuration and, therefore, other various suitable circuit configurations can be used and are within the scope of the present disclosure.

With some volatile compositions (for instance those comprising fragrances) it may be helpful to adjust the fan speed, frequency of run time, or on/off time to compensate for the changing volatile composition formulation as high vapor pressure volatile composition raw materials will evaporate more quickly than low vapor pressure raw materials. In this case it may optionally be desirable to have the controller operate the fan more frequently as the volatile composition is evaporated over a period of many days. For instance in one non-limiting example, the fan could run at 10% duty cycle for the first 10 days of usage but then slowly increase up to about 30% to about 40% duty cycle from days 11 up to 60 days. In this way the fan frequency or duration can be increased to compensate for potentially a decline in fragrance intensity. By adjusting for the age, it is possible to deliver a more consistent scent intensity even as the fragrance amount and mixture of high to low vapor pressure components is changing with time. Further as the replaceable unit 32 or 32' or 232 ages, the controller 30 or 230 could also use a motion detector to know when a user is operating the vehicle and could then adjust the fan operating conditions differently for when the vehicle is in operation versus when the vehicle is in a parked condition for several minutes or hours.

One non-limiting example of a means of keeping track of run time of the replaceable unit 32 or 32' or 232 is to monitor the voltage of the battery associated with the replaceable unit 32 or 32' or 232. For instance, a new AA battery may be 1.60 Volts to about 1.65 Volts while a AA battery that was used for thirty days might have a voltage of about 1.2 Volts to about 1.45 Volts. By monitoring the voltage of the battery, the controller 30 or 230 can recognize the life of the replaceable unit 32 or 32' or 232 and can adjust operating conditions to deliver a consistent scent experience over the life of the replaceable unit 32 or 32' or 232.

Another non-limiting example of a means to monitor time, is to start a timer when the replaceable unit 32 or 32' or 232 is inserted and to keep track of hours/minutes that the fan has operated. As mentioned above, the fan time could be adjusted as the product ages to deliver a more consistent scent experience.

In the instance where the battery voltage or run time is viewed as the indicator of the full life of the replaceable unit 32 or 32' or 232, the controller 30 or 230 could be programmed to provide a signal to the user such as turning on a red light or provide a flashing light to indicate that the replaceable unit 32 or 32' or 232 is empty and/or needs to be replaced.

Figure 20:
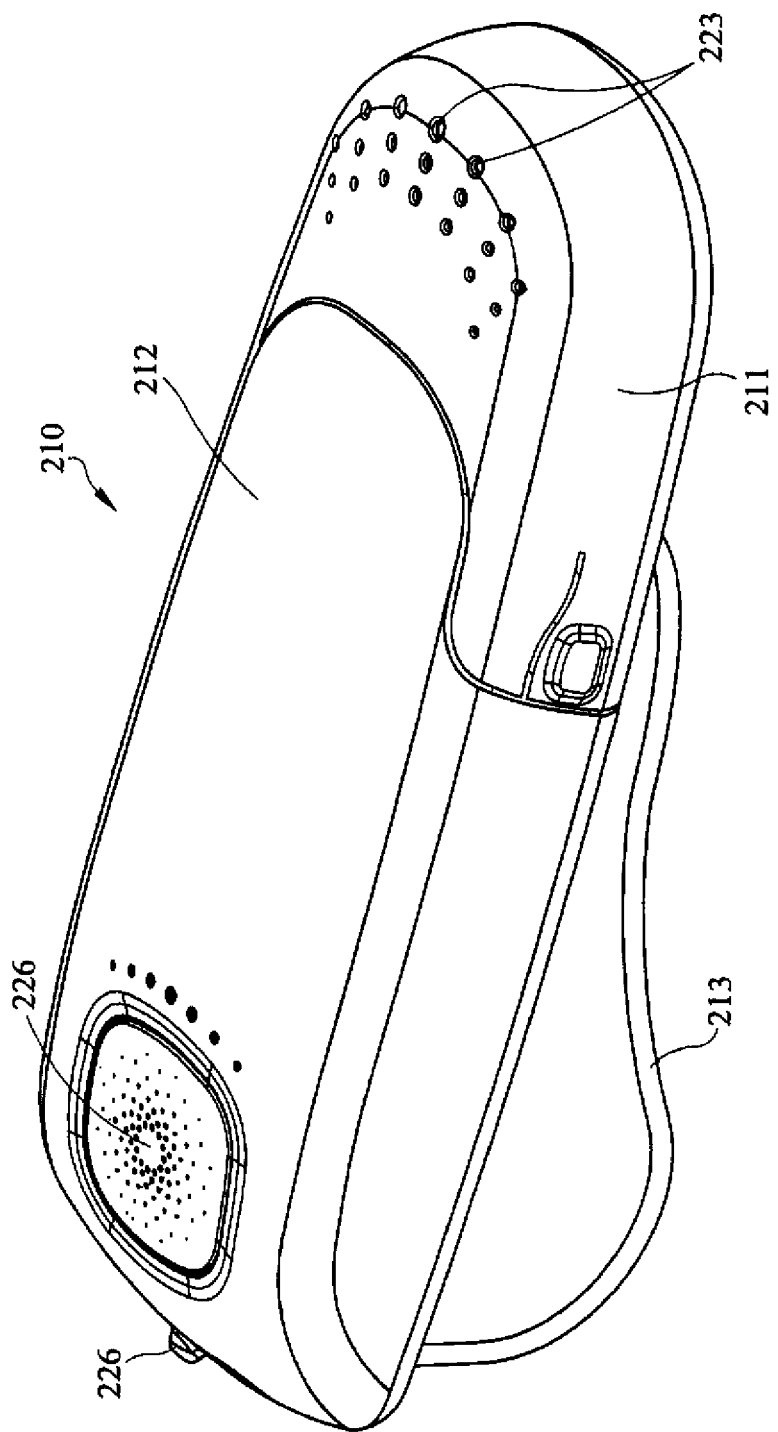
FIG. 20 is a perspective view of a volatile composition dispenser in accordance with one non-limiting embodiment.
Figure 21:
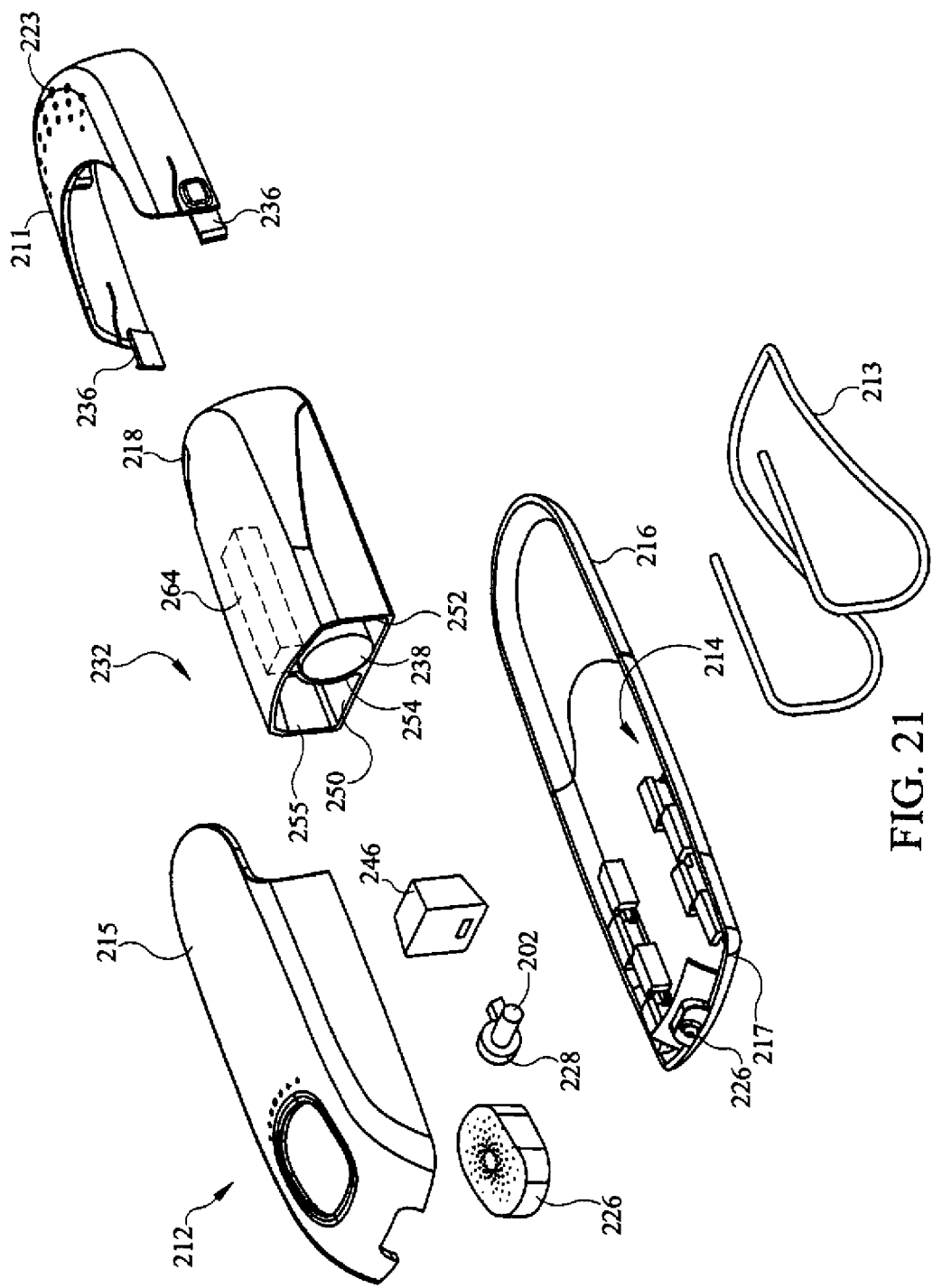
FIG. 21 is an exploded perspective view of the volatile composition dispenser of FIG. 20 in accordance with one non-limiting embodiment.
Figure 22:
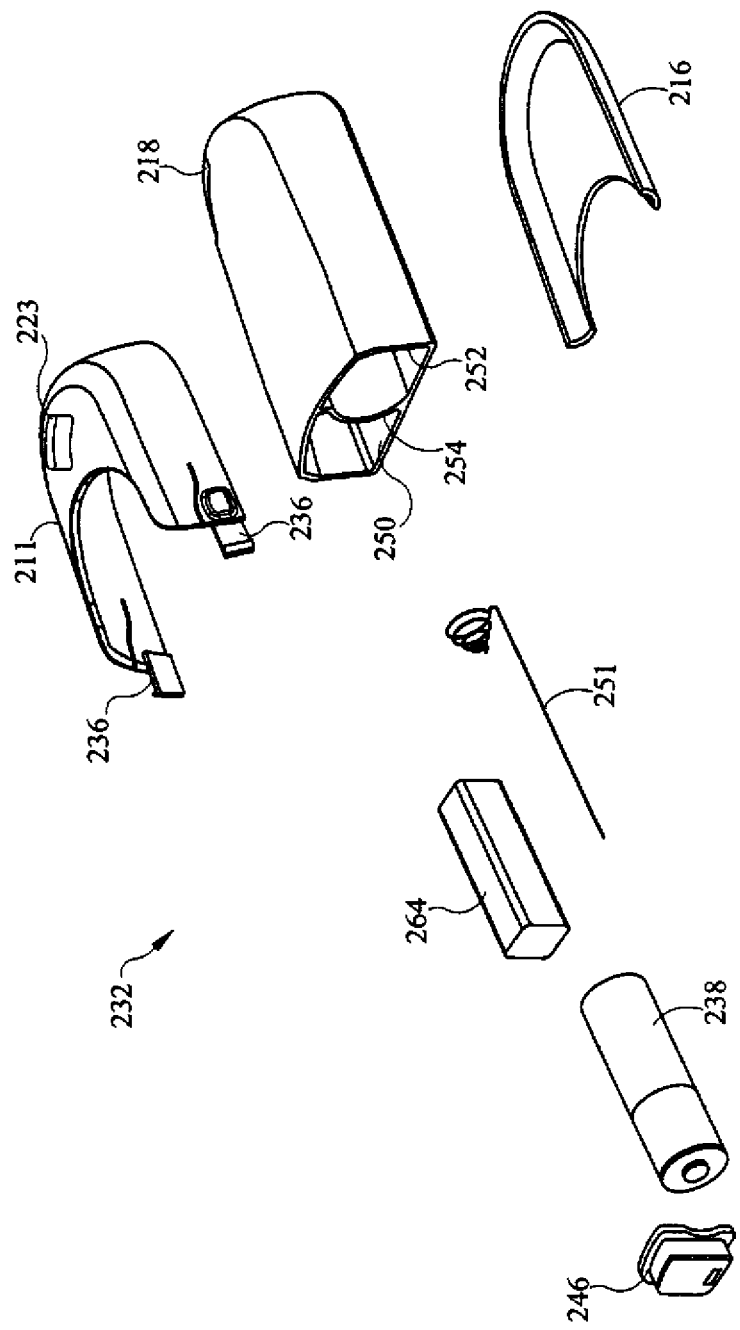
FIG. 22 is an exploded perspective view of a replaceable unit of a volatile composition dispenser in accordance with one non-limiting embodiment.
Figure 23:
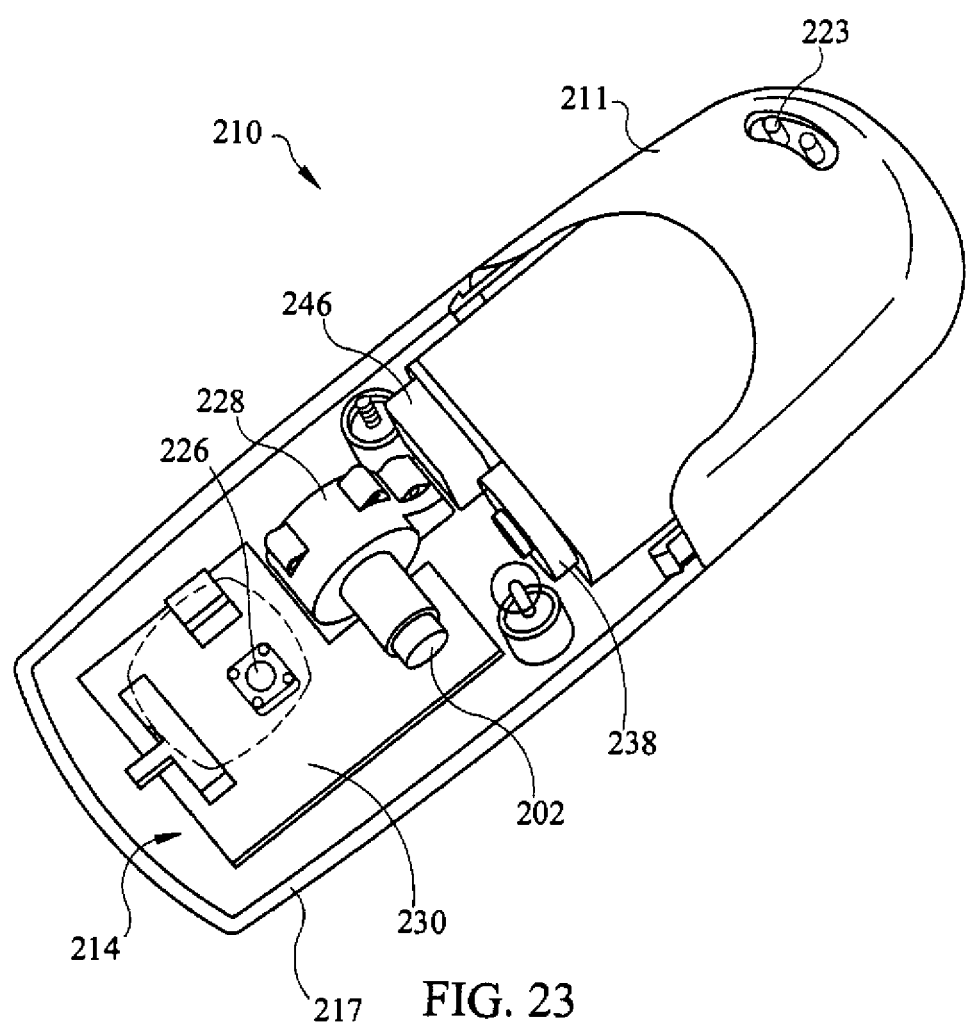
FIG. 23 is a perspective view of a volatile composition dispenser with a portion of its housing removed in accordance with one non-limiting embodiment.

In various embodiments, referring to FIGS. 20-22, a volatile composition dispenser 210 can comprise a housing 212 comprising a top shell 215 and a bottom shell 217. When the top shell 215 and bottom shell 217 are joined together, they can define a cavity 214. In various embodiments, the volatile composition dispenser 210 can comprise a clip 213 and a replaceable unit 232. The replaceable unit 232 can comprise an optional dividing wall 254. The replaceable unit 232 can comprise a power source 252, a lead 251, a volatile composition container 250 sealed with a volatile composition container cap 246. A high surface area material 264 can be positioned within the volatile composition container 250, or the high surface area material can be in a separate container that is received within the volatile composition container 250, similar to the previously discussed embodiments. As with previous embodiments, the separate container can be attached to or bundled with a power source 238. As shown illustrated in FIG. 21, with the housing 212 removed for illustration purposes, the volatile composition dispenser 210 can comprise similar internal components as those discussed above with respect to other various embodiments, such as an actuator 228, a controller 230, a motor 202, and/or a button assemblies or switches 226. In various embodiments, the volatile composition dispenser 210 may comprise a user feedback module comprising at least one indicator comprising a plurality of light sources and/or a translucent portion in the housing 212. In one non-limiting embodiment, the button assembly 226 can comprise at least a translucent portion configured to allow a light source, or plurality of light sources positioned within the cavity 214, to illuminate the button 226. As will be appreciated, different colors of lights, or blinking patterns, can be employed to convey various information to the user. For example, certain light patterns and/or configurations can denote the dose amount, the dose frequency, the power level of the power source 238, and/or the volatile composition level, for example. In one non-limiting embodiment, the volatile composition dispenser 210 can comprise a holder 211. The holder 211 can have at least one latch 236, or other connection device, to secure the holder 211 to the housing 212. The volatile composition dispenser 210 may comprise a bottom pan 216. When the holder 211 and the bottom pan 216 are positioned and/or slid over the replaceable unit 232, and the holder 211 is secured to the housing 212, the replaceable unit 232 can be maintained in a proper orientation and/or position in relation to the housing 212. When the user wishes to exchange the replaceable unit 232, the holder 211 can be detached from the housing 212 to allow for removal of the replaceable unit 232. As will be appreciated by those of skill in the art upon consideration of the present disclosure, the holder 211 and the bottom pan 216 can comprise any suitable configuration for securing the replaceable unit 232 to the housing 212, such as a sleeve, a strap, and/or a buckle, for example. In various embodiments, the bottom pan 216 may be eliminated and/or can be formed with the holder 211, for example. The holder 211 can maintain the placement of the replaceable unit 232 relative to the actuator 228 and power source 238 during use. The replaceable unit 232 can have at least one outlet orifice 218. The sizing, geometry, and/or configuration of the orifice 218 can be determined similar to the configuration considerations provided for the outlet orifice 18 discussed above. In one non-limiting embodiment, the holder 211 can comprise one or more orifices 223 to allow for the volatile composition contained within the volatile composition container 250 to be expelled from the volatile composition dispenser 210 during operation. In one non-limiting embodiment, an additional orifice can be provided proximate to where the clip 213 interfaces with the bottom shell 217 to allow air to travel from the atmosphere surrounding the dispenser 210 into the dispenser 210 and into the actuator 228.

Similar to the volatile composition container 50 discussed above, in various embodiments, the volatile composition container 250 can comprise a high surface area material, such as a porous material and/or a wick, for example, and a space configured to receive a vapor phase volatile composition therein. In various embodiments, similar to the one or more projections 84 illustrated in FIG. 10, a side wall 255 can comprise one or more projections, such as continuous or non-continuous ribs, elongate members, pins, for example, extending therefrom and configured to maintain the material in place within the volatile composition container 250, for example. In various embodiments, the high surface area material 264 may comprise projections. In various embodiments, similar to previously discussed embodiments, the one or more projections can allow the volume of air to pass between them and the material. The operation of the dispenser 210 can be similar in nature to the embodiments previously discussed. In various embodiments, the replaceable unit 32' can also be used with this embodiment.

The present disclosure, in part, can comprise a method of dispensing a volatile composition comprising providing a replaceable unit comprising a power source and a volatile composition container comprising a volatile composition. The method can further comprise providing a fan, such as a centrifugal fan, for example, powered by the power source and in fluid communication with the volatile composition container and evaporating a portion of the volatile composition within the volatile composition container. The method can also comprise using the centrifugal fan to intermittently force a volume of air at least partially through the volatile composition container to expel at least most of the evaporated portion of the volatile composition from the volatile composition container. As provided, when the volatile composition and/or the power source has been depleted, the volatile composition and/or the power source can be replaced. In some embodiments, a bundle comprising a volatile composition container containing a volatile composition and a power source is provided. The bundle can be inserted into a shell and attached to the housing and/or a portion of the housing (not illustrated). In some embodiments, a volatile composition and a power source can be provided that each separately can be placed into a shell and attached to the housing or inserted into a portion of the housing (not illustrated). In some embodiments, a shell containing a volatile composition and a power source can be provided to the user that attaches directly to the housing. In some embodiments, a volatile composition and a power source can be provided to the user and placed directly in the housing. In other embodiments, other suitable configurations or implementations can be used.

Although the various volatile composition dispensers disclosed herein have been discussed for use in a vehicle, those of ordinary skill in the art will recognize other uses for the dispensers in other environments. In one non-limiting embodiment, the volatile composition dispensers can be used to dispense insecticide at a camp site and/or within a tent or cabin, for example. In other various embodiments, the volatile composition dispensers can be used in a home, a workplace, a locker, a storage space, and/or any other suitable place or environment where the volatile composition dispenser would have utility to a user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method of dispensing a volatile composition, the method comprising the steps of:
   providing a volatile composition dispenser comprising a replaceable unit that is releasably connected with the volatile composition dispenser, the replaceable unit comprising a power source, a volatile composition container comprising the volatile composition in at least partially a liquid phase, and a high surface area material contained within the volatile composition container, wherein the high surface area material comprises at least one surface;
   providing a fan powered by said power source and in fluid communication with said volatile composition container;
   evaporating a portion of said volatile composition within said volatile composition container;
   using said fan to intermittently force a volume of air at least partially through said volatile composition container to expel at least most of the evaporated portion of said volatile composition from said volatile composition container at a flow rate of about 2 $cm^3$/second to about 20 $cm^3$/second.

2. The method of claim 1, wherein the replaceable unit comprises a shell that contains both the volatile composition container and the power source.

3. The method of claim 1, wherein said volatile composition container comprises an inner wall and at least one projection extending into said volatile composition container from said inner wall, wherein said at least one projection is configured to engage said high surface area material to maintain said high surface area material at a distance away from said inner wall.

4. The method of claim 3, wherein said volatile composition container comprises at least one space defined intermediate said inner wall and the surfaces of said high surface area material, wherein said at least one space is configured to receive the evaporated portion of the volatile composition.

5. The method of claim 1, wherein said volatile composition container comprises at least one first orifice configured to receive said volume of air from said fan and comprises at least one second orifice configured to expel at least a portion of said volume of air and a portion of the evaporated portion of the volatile composition from said volatile composition container to the atmosphere.

6. The method of claim 5, wherein said at least one first orifice and said at least one second orifice each have a cross-sectional area in the range of about 0.007 cm$^2$ to about 0.50 cm$^2$.

7. A method of dispensing a volatile composition, the method comprising the steps of:
providing a volatile composition dispenser comprising a housing and an actuator disposed within the housing, the volatile composition dispenser comprising a replaceable unit connected to the housing, wherein the replaceable unit comprises a power source, a volatile composition container comprising the volatile composition, and a high surface area material contained within the volatile composition container, wherein the actuator is in fluid communication with the volatile composition container and electrical communication with the power source, wherein a gap is formed between the volatile composition container and the high surface area material, wherein at least a portion of the gap is about 0.5 mm to about 3 mm;
evaporating a portion of said volatile composition within said volatile composition container; and
using said actuator to intermittently force a volume of air at least partially through said volatile composition container to expel the evaporated portion of said volatile composition from said volatile composition container.

8. The method of claim 7 further comprising the steps of:
removing the replaceable unit; and
inserting a new replaceable unit, the new replaceable unit comprising a power source, a volatile composition container comprising the volatile composition in at least partially a liquid phase, and a high surface area material contained within the volatile composition container.

9. The method of claim 7, wherein the replaceable unit comprises a shell that contains both the volatile composition container and the power source.

10. The method of claim 7, wherein said volatile composition container comprises an inner wall and at least one projection extending into said volatile composition container from said inner wall, wherein said at least one projection is configured to engage said high surface area material to maintain said high surface area material at a distance away from said inner wall.

11. The method of claim 10, wherein said volatile composition container comprises at least one space defined intermediate said inner wall and the surfaces of said high surface area material, wherein said at least one space is configured to receive the evaporated portion of the volatile composition.

12. The method of claim 7, wherein said volatile composition container comprises at least one first orifice configured to receive said volume of air and comprises at least one second orifice configured to expel at least a portion of said volume of air and a portion of the evaporated portion of the volatile composition from said volatile composition container to the atmosphere.

13. The method of claim 12, wherein said at least one first orifice and said at least one second orifice each have a cross-sectional area in the range of about 0.007 cm$^2$ to about 0.50 cm$^2$.

14. A method of dispensing a volatile composition, the method comprising the steps of:
providing a dispenser comprising a housing and a replaceable unit positioned at least partially within the housing, the replaceable unit comprising a power source, a volatile composition container comprising the volatile composition in at least partially a liquid phase, and a high surface area material contained within the volatile composition container, wherein the high surface area material comprises at least one surface, wherein said volatile composition container comprises at least one first orifice configured to receive said volume of air from said fan and comprises at least one second orifice configured to expel at least a portion of said volume of air from said volatile composition container to the atmosphere, wherein said at least one first orifice and said at least one second orifice each have a cross-sectional area in the range of about 0.007 cm$^2$ to about 0.50 cm$^2$;
providing a fan powered by said power source and in fluid communication with said volatile composition container;
evaporating a portion of said volatile composition within said volatile composition container; and
using said fan to intermittently force a volume of air at least partially through said volatile composition container to expel at least most of the evaporated portion of said volatile composition from said volatile composition container, wherein a flow path of the volume of air at least partially through the volatile composition container is substantially along the at least one surface of the high surface area material.

15. The method of claim 14 wherein said volatile composition container comprises an inner wall and at least one projection extending into said volatile composition container from said inner wall, wherein said at least one projection is configured to engage said high surface area material to maintain said high surface area material at a distance away from said inner wall.

16. The method of claim 15 wherein said volatile composition container comprises at least one space defined intermediate said inner wall and the surfaces of said high surface area material, wherein said at least one space is configured to receive the evaporated portion of volatile composition.

* * * * *